United States Patent [19]
Ho et al.

[11] Patent Number: 5,665,359
[45] Date of Patent: Sep. 9, 1997

[54] METHOD AND COMPOSITIONS FOR LOWERING BLOOD LIPIDS

[76] Inventors: Walter Kwok Keung Ho, Flat 12B, Residence 13, Chinese University of Hong Kong; Hson-Mou Chang, Flat 4D, Lily Court, World Wide Gardens, both of Shatin, N.T., Hong Kong; Chi-Ming Lee, 100 Pyler City Rd., Orange, Conn. 06477

[21] Appl. No.: 235,550

[22] Filed: Apr. 29, 1994

[51] Int. Cl.[6] .................................... A61K 35/78
[52] U.S. Cl. ........................ 424/195.1; 514/424
[58] Field of Search ................. 424/195.1, 514

[56] References Cited

U.S. PATENT DOCUMENTS

| | | | |
|---|---|---|---|
| 4,522,811 | 6/1985 | Eppstein et al. | 514/2 |
| 5,240,732 | 8/1993 | Ueda | 426/597 |

OTHER PUBLICATIONS

Allain, Charles C., et al., "Enzymatic Determination of Total Serum Cholesterol," *Clin. Chem.*, 20(4):470–475 (1974).

Beitz, J. and H. J. Mest, "A New Derivatives of Trapidil (AR 12456) As a Potentially New Antiatherscleorotic Drug," *Cardio. Vasc. Drug. Rev.* 9(4):385–397 (Winter 1991).

Bierman, E.L., "Disorder of the Vascular System: Ahterosclerosis and Other Forms of ArterioSclerosis," in *Harrison's Principles of Internal Medicine* 1814–1824, E. Braunwald et al., Ed. (1987).

Brown, M.S., and J.L. Goldstein, "The Hyperlipoproteinemias and Other Disorders of Lipid Metabolism," in *Harrsion's Principles of Internal Medicine* 1658–1661, E. Braunwald et al., Ed. (1987).

Dai, Y.-R., et al., "Effect of Extracts of Some Medicinal Plants on Superoxide Dismutase Activity in Mice," *Planta Medica* 53(3):309–310 (Jun. 1987).

Fruchart, J.-C., "Mecanismes d'Action des Hypolipidemiants," *J. Pharm. Belg.* 47(4):345–350 (1992). [Abstracts in English].

Henninghausen, L., et al., "Interaction of Protein with DNA in Vitro," *Methods in Enzymology* 152:721–735 (1987).

Itakura, K. et al., "Synthesis and Use of Synthetic Oligonucleotides," *Ann. Rev. Biochem.* 53:323–356 (1984).

Paoletti, R., and A. Poli, "Pharmacological Control of Serum Lipid Levels: Currently Available Drugs," (Supp. E) *Eur. Heart J.* 8:87–91 (Aug. 1987).

Paoletti, R. et al., "Modulation of LDL Receptors by Drugs Affecting Calcium Metabolism," *Biotechnol. and Clin. Med.* 45–55, A, Albertini et al. eds., Raven Press, Ltd., New York (1987).

Paoletti, R., and F. Bernini, "Calcium Antagonists and Hypocholesterolemic Drugs in the Regulation of LDL Receptors," *Actual. Chim. Ther.* 15:35–40 (1988).

Qin, W., et al., "Regulation of HMG–CoA Reductase, Apoprotein–B and LDL Receptor Gene Expression by the Hypocholestreolemic Drugs Simvastatin and Ciprofibrate in Hep G2, Human and Rat Hepatocytes," *Biochim. Biophys. Acta* 1127:57–66 (1992). (Also in *Mol. Biol. Atherosclerosis* 599–602, Proc. Eur. Atheroscler. Soc. Meeting, 1992.).

Shepard, J., et al., "Drug–induced Modulation of Low–Denisty Lipoprotein Receptor in Man," *Brit. Hert J.* 47(2):197 (Feb. 1982).

Shephard, J., and C.J. Packard, "Pharmacologic Modulation of the Low Density Lipoprotein Receptor Pathway," *Recent Aspects of Diagnosis and Treatment of Lipoprotein Disorders: Impact on Prevention of Antiatheroscleorotic Diseases* 265–271 (Alan R. Liss, Inc. 1988) ( Proceedings of a meeting, Vienna, Austria, Aug. 21–23, 1986).

Snarry, W. M., et al., "The Determination of Total Lipides in Blood Serum," *J. Biol. Chem.* 213:69–76 (Baltimore 1955).

Südhof, T. C., et al., "Three Direct Repeats and a TATA–like Sequence Are Required for Regulated Expression of the Human Low Density Lipoprotein Receptor Gene," *J. Biol. Chem.*, 262(22):10773–10779 (Aug. 5, 1987).

Wade, D.P. et al., "Hormonal Regulation of Low–Density Lipoprotein (LDL) Receptor Activity in Human Hepatoma HepG2 Cells: Insulin Increases LDL Receptor Activity and Diminishes its Suppression By Exogenous LDL," *Eur. J. Biochem.* 174(1):213–218 (May 16, 1988).

Weilang, Weng, et al., "Therapeutic Effect of *Crataegers pinnatifida* or 46 Cases of Angina Pectoris —A Double Blind Study," *J. Traditional Chinese Med.* 4(4):293–294 (1984).

*Primary Examiner*—John W. Rollins
*Attorney, Agent, or Firm*—Arnall Golden & Gregory

[57] ABSTRACT

It has been discovered that the Chinese fruit known as shanzha, and extracts and purified component derived therefrom, can be administered orally to animals to reduce levels of cholesterol in the blood. The mechanism of action is believed to include the "up-regulation" of LDL receptors on cell surfaces and inhibition of transcription factors for sterol responsive genes. Examples demonstrate the isolation of active components and extracts, potential mechanisms of action in animals and cell culture, and conditions promoting retention of activity during storage.

14 Claims, 11 Drawing Sheets

FIG. 1

PREPARATION OF SHANZHA EXTRACT

FRESH FRUIT SLICED AND DRIED

1 Kg OF DRIED FRUIT BOILED UNDER SLOW HEAT IN 3.5 L OF WATER FOR 2 HOURS

INSOLUBLE MATERIALS WERE REMOVED BY FILTERING THROUGH CHEESE CLOTH

FINAL VOLUME OF LIQUID OBTAINED WAS APPROXIMATELY 2 L

MATERIAL CLARIFIED BY CENTRIFUGATION 5000 rpm, 20 MINUTES

CLEARED SUPERNATANT WAS ROTARY EVAPORATED AT 50 TO 60°C UNTIL VOLUME WAS REDUCED BY 40 %

CONCENTRATED MATERIALS WERE THEN FROZEN AT −70°C AND LYOPHILIZED

THE FINAL EXTRACT OBTAINED IS A FULLY LIGHT BROWN MATERIAL WITH NO SIGN OF CARAMELIZATION (FIG. 1B) AMOUNT OF EXTRACT IS APPROXIMATELY 0.16 Kg

FIG. 2
PURIFICATION OF ACTIVE INGREDIENT FROM SHANZHA
✶ INDICATES ACTIVE FRACTION 500 gm DRIED FRUIT REFLUX IN 50% ETHANOL FOR 2 HOURS
|
FILTERED AND VACCUM DRIED (112 gm)
├── CHLOROFORM K1 Fx (2.1 gm)
└── Water ✶
    ├── ETHYLACETATE ✶ K2 Fx (5.5 gm)
    └── Water
        └── n-butanol K3 Fx (14 gm) ── Water ETHYLACETATE K2 Fx → SILICA GEL COLUMN:
- K2-1 (0% MeOH)
- K2-2 (5%)
- K2-3 (10%) ✶
- K2-4 (20%)

(1 gm) → C-18 REVERSE PHASE OPEN COLUMN:
- K231 & K232 (25% acetonitrile)
- K233 (30% Acn) ✶
- K234 (45% Acn)

(SEE CHROMATOGRAM IN FIGURE 3A)

(74 mg) → HPLC ON C-18 REVERSE PHASE (0-40% Acn gradient):
- K233-1
- K233-2
- K233-3 ✶
- K233-4

(SEE CHROMATOGRAM IN FIGURE 3B)

PURIFIED FRACTION K233-3 (9.5 mg)

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: synthetic DNA ( x ) PUBLICATION INFORMATION:
        ( A ) AUTHORS: Sudhoff, et al.
        ( C ) JOURNAL: Biol. Chem.
        ( D ) VOLUME: 262
        ( F ) PAGES: 10773-10779
        ( G ) DATE: 1987

( x i ) SEQUENCE DESCRIPTION: SEQ ID NO:1:

AAAATCACCC CACTGC          1 6

METHOD AND COMPOSITIONS FOR LOWERING BLOOD LIPIDS

BACKGROUND OF THE INVENTION

The present invention is generally in the area of compositions for lowering blood lipids, and specifically relates to compositions derived from shanzha fruit.

Hyperlipidemias, particularly hypercholesterolemia and the hyperlipoproteinemias, are among the most potent risk factors in the causation of atherosclerosis. Hyperlipoproteinemias are also implicated in the development of pancreatitis. A long-established theory suggests that the higher the circulating levels of low density lipoprotein, the more likely they are to gain entrance to the arterial wall and cause atherosclerosis. (M.S. Brown and J. L. Goldstein, "The Hyperlipoproteinemias and Other Disorders of Lipid Metabolism," in *Harrison's Principles of Internal Medicine* 1650–1661, (E. Braunwald et al. 1987)).

Lipoproteins, including intermediate density lipoprotein (IDL) and low density lipoprotein (LDL), are the major carriers for triglycerides and cholesterol, in the form of cholesteryl esters, in the plasma. The core of an IDL or LDL particle is cholesterol rich. About three-fourths of the total cholesterol in normal human plasma is contained in LDL particles. In the liver, LDL is taken up from the blood through binding to LDL receptors on hepatocytes. In humans, 70 to 80 per cent of LDL is removed from the plasma each day by the LDL receptor pathway in hepatocytes.

Some of the cholesterol from LDL particles is used by hepatocytes in the synthesis of bile acids, which are excreted along with some free cholesterol through the biliary system into the intestine, and some is used in the cell for synthesis of cellular membranous organelles or distributed to other tissues for use in organelle and steroid hormone synthesis. If uptake is blocked at the receptor level, cholesterol accumulates in the blood and can contribute to atherosclerosis.

Cells needing cholesterol for membrane synthesis make LDL receptors and insert them into the cell membrane, where they associate with coated pits. When LDL receptors bind LDL, the coated pits pinch off into the cytoplasm, form coated vesicles, and thereby internalize LDL into the cell. LDL receptors are subsequently recycled to the cell membrane, and the cholesterol is used in membrane synthesis. If too much cholesterol accumulates in a cell, the cell's own synthesis of cholesterol and LDL receptor protein is shut down. Then less cholesterol is taken up by the cell.

In hypercholesterolemia, the increase in the blood cholesterol level is associated mainly with a rise in LDL concentrations. However, the specific causes of hypercholesterolemia are complicated, varied, and largely, unknown. At least one kind of hypercholesterolemia is caused by a mutation in the gene for the LDL receptor. Both heterozygotes and homozygotes for the defect manifest a significant elevation in the concentration of total plasma cholesterol, which is attributable to an elevation in the level of serum LDL.

Reduction of hypercholesterolemia results in a delayed onset of atherosclerosis and a decrease in progression of atherosclerosis, thus reducing the risk of coronary heart disease in humans and other primates. Specifically, there is evidence in animals, most notably primates, that relatively complicated plaques induced by hyperlipidemia will regress, and that further progression of atherosclerosis will cease when hyperlipidemia is removed. Therefore, efforts to prevent atherogenesis, to interrupt progression, and perhaps to promote regression of existing lesions by risk factor reduction are warranted. E. L. Bierman, "Disorders of the Vascular System: Atherosclerosis and Other Forms of Arteriosclerosis," in *Harrison's Principles of Internal Medicine* 1014–1024, (E. Braunwald et al. 1987).

Some forms of hyperlipidemia, including hypercholesterolemia, are potentially partially reversible with current techniques of preventive management. However, none of the current techniques is completely successful and many are associated with unwanted side effects and complications. Dietary therapy is usually recommended for patients with hypercholesterolemia but is not always effective. Methods that result in an increased production of LDL receptors, thus allowing the liver to take up more LDL from blood, have also been proposed. For example, bile acid binding resins, such as cholestyramine, may be used to trap the bile acids excreted by the liver. When bile acids are depleted, the liver responds by converting additional cholesterol into bile acids. To step up the synthesis of bile acids, an enhanced production of LDL receptors by the liver occurs, which in turn lowers the plasma level of LDL. One complication of this approach to treating high serum cholesterol by reduction of bile acids is that the liver may also respond to bile acid depletion by enhancing cholesterol synthesis. Bile acid binding resins may also cause gastrointestinal bloating, cramps, and constipation.

Methods for treating disease states associated with high blood levels of lipids by increasing the number of LDL receptors in hepatocytes by a class of drugs that exhibit 3-hydroxy-3-methylglutaryl coenzyme A (HMGCoA reductase), an enzyme involved in cholesterol synthesis, have also been proposed. However, long term administration of HMGCoA reductase inhibitor may lead to a suppression of cholesterol synthesis that in turn may affect the availability of precursor for essential steroid hormones such as mineralocorticoids, glucocorticoids, and the sex hormones. Further, some patients using HMGCoA reductase inhibitor have developed cataracts prematurely. Accordingly, what is needed are other effective methods and compositions for use in lowering blood lipid levels and in treating disease states associated with high levels of blood lipids.

It is therefore an object of the present invention to provide compositions and methods of use to treat high blood lipid or lipoprotein levels and disease states related to each of these.

It is a further object of the present invention to provide compositions and methods of use to treat hypercholesterolemia and related disease states, such as atherosclerosis.

SUMMARY OF THE INVENTION

It has been discovered that the Chinese fruit known as shanzha, and extracts and purified component derived therefrom, can be administered orally to animals to reduce levels of cholesterol in the blood. The mechanism of action is believed to include the "up-regulation" of LDL receptors on cell surfaces.

Examples demonstrate the isolation of active components and extracts, potential mechanisms of action in animals and cell culture, and conditions promoting retention of activity during storage.

BRIEF DESCRIPTION OF THE DRAWINGS

FIG. 1 is a flow chart illustrating the steps used in the preparation of a shanzha extract. The liquid obtained from boiling dried shanzha fruit under slow heat in water for two hours is centrifuged. The cleared supernatant is then rotary evaporated to produce concentrated materials that are frozen at −70° C. and lyophilized, forming a fluffy light brown shanzha extract.

FIG. 2 is a flow chart illustrating the steps used in an exemplary method for purification of the active component (s) in the crude shanzha extract of FIG. 1. The dried fruit reflux is extracted in 50% ethanol for two hours, and the ethanol extract is filtered, vacuum dried, and then extracted in a chloroform/water mixture. The resulting water extract is extracted in an ethylacetate/water mixture, and this water extract is further extracted in an n-butanol/water mixture. The ethylacetate extract is further purified by gel filtration chromatography, followed by reverse phase open column chromatography and high performance liquid chromatography, to form a partially purified fraction (K233-3).

FIG. 3a is a C-18 reverse phase open column chromatogram of the K2-3 fraction, read at O.D. 254, in which the solvent was acetonitrile (at concentrations of 25%, 30%, and 45%), identifying the K233 fraction at 30% acetonitrile. FIG. 3b is an HPLC chromatogram of the K233 fraction on a C-18 reverse phase column, identifying the K233-3 fraction at position 3.

DETAILED DESCRIPTION OF THE INVENTION

Figure 3A:
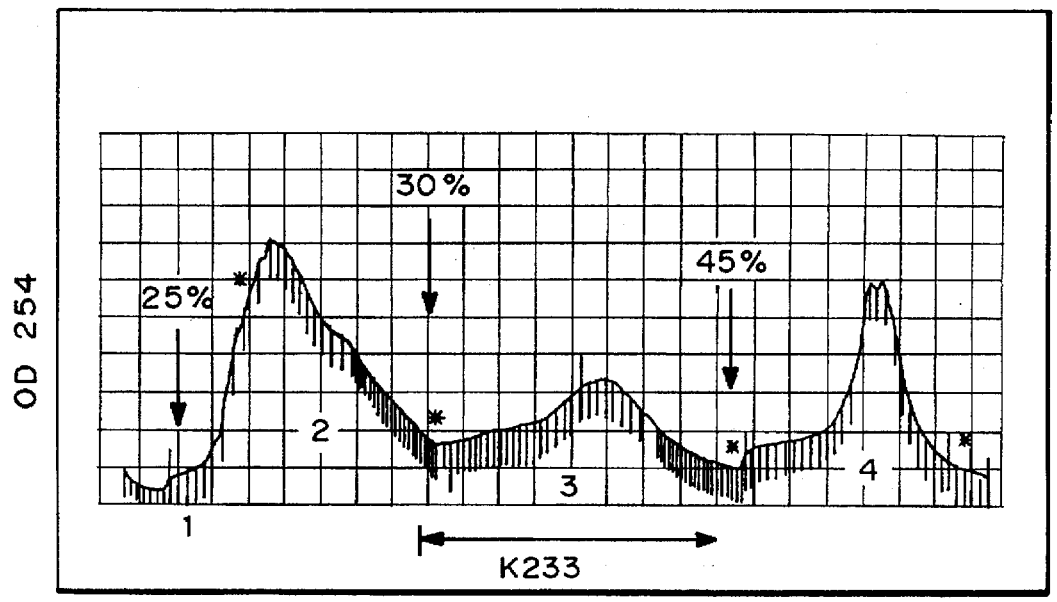
FIGS. 3a and 3b show chromatograms resulting from steps in the partial purification of the active component(s) of the crude shanzha extract.
Figure 3B:
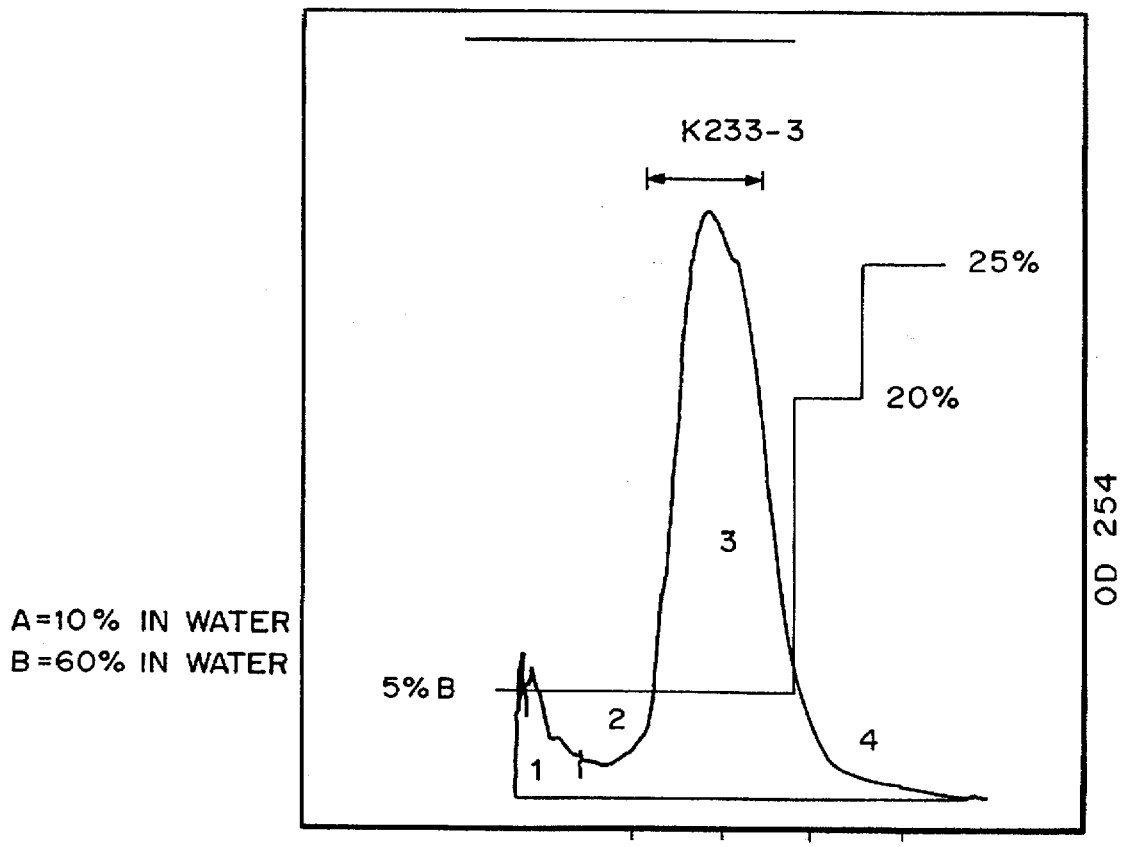

The fruits of the *Fructus crataegi* or *Crataegus pinnatifida* plant, shanzha, have been used in traditional Chinese medicine as an aid to digestion and to treat circulatory problems related to blood clotting. The drinking of shanzha Juice after a heavy meal is a common practice in China.

It has been discovered that oral administration of the juice of the shanzha fruit or active extracts thereof has a hypocholesterolemic effect in animals. "Shanzha," as used herein, refers to the fruit of the *Fructus crataegi* or *Crataegus pinnatifida* plants and includes the juice of the shanzha fruit or active extracts thereof. "Active extracts thereof" refers to extracts of the shanzha fruit that are effective in lowering the level of lipids, particularly cholesterol, in blood.

Shanzha apparently lower serum cholesterol through inhibition of LDL receptor down-regulation. Typically, in a hypercholesterolemic subject, the LDL receptor is down-regulated, and the further removal of intermediate density lipoproteins (IDL) and LDL from the plasma is prevented. By inhibiting this down-regulation, shanzha enables hepatocytes to take up more LDL from the blood. Cholesterol in the hepatocytes is then cleared through excretion as bile acids or free cholesterol into the biliary system, which drains into the small intestine. This mode of action in reducing serum LDL complements that of the HMGCoA reductase inhibitors, since shanzha can act in combination with these drugs to produce an even more powerful method of treatment of hypercholesterolemia.

This discovery allows shanzha to be used as a therapeutic agent to treat hyperlipidemia, hyperlipoproteinemia, hypercholesterolemia, and diseases associated with each of these, such as atherosclerosis and pancreatitis.

Definitions

"Hyperlipidemia," as used herein, is a general term for elevated concentrations of any or all of the lipids in the plasma, and includes hyperlipoproteinemia and hypercholesterolemia.

"Hyperlipoproteinemia," as used herein, refers to an excess of lipoproteins in the blood occurring as an acquired or familial condition due to a disorder of lipoprotein metabolism. Familial hyperlipoproteinemias include, for example, low density lipoprotein (LDL) receptor disorders, several types of familial hypercholesterolemia, and hypertriglyceridemia. Acquired hyperlipoproteinemias include, for example, the condition induced by diet.

"Hypercholesterolemia," as used herein, refers to an excess of cholesterol in the blood and may be familial, such as that associated with a defect in the LDL receptor, or acquired.

"Down-regulation" of receptors, as used herein, refers to the process whereby a stimulus, such as the binding of the receptor to its ligand, leads to a decrease in the concentration of receptors on the cell surface. In LDL metabolism, the binding of LDL to surface receptors, followed by internalization of the receptor-LDL complex and release of cholesterol in the cell, increases the intracellular concentration of cholesterol and may decrease the synthesis of additional complementary receptor molecules and insertion in the cell membrane. "Up-regulation" of receptors, as used herein, refers to the process whereby a stimulus, such as a decrease in the intracellular level of cholesterol, leads to an increase in the concentration of receptors on the cell surface.

Compositions and Reagents (1) Shanzha Fruit and Juice Extract.

Shanzha fruit or fruit juice can be used to lower serum cholesterol. However, the effective amount to lower blood cholesterol of raw or unprocessed fruit is significantly greater than the effective amount of a concentrated extract or purified active components.

(2) Preparation of an Active Shanzha Extract from Natural Sources.

As shown by the flow chart in FIG. 1 an active extract of shanzha can be prepared from fresh shanzha fruit by extracting the fruit in a liquid and concentrating the resulting juice to form a concentrated extract. In a preferred embodiment for preparation of an extract, fresh shanzha fruit is sliced, dried, and boiled under slow heat in a solvent liquid such as water. Insoluble materials are removed, for example by filtration, and the remaining product is clarified by centrifugation or other means. The cleared supernatant is concentrated and lyophilized for storage and use.

It is important that the fruit and extract be stored under conditions in which the active ingredients do not loose their efficacy, as, for example, under refrigeration and/or in the presence of antioxidants and bacteriostatic agents. Suitable materials for enhancing storage and effective concentrations of these are well known to those skilled in the art of fruit, fruit extract, and pharmaceutical preparation.

(3) Preparation of Purified or Partially Purified Active Extracts of Shanzha.

Water, alcohol, and organic solvent extracts of active components of shanzha can be prepared. The compounds in these extracts can then be further purified using standard techniques such as chromatography on ion exchange columns or high performance liquid chromatography (HPLC).

The flow chart in FIG. 2 shows one embodiment of a method for preparing partially purified extracts. The dried fruit is extracted with an aqueous alcohol solution such as 50% ethanol, and the extract is filtered and dried. The ethanol extract is extracted into a series of organic solvent/aqueous mixtures of increasing polarity. For example, the 50% ethanol extract can be extracted into a chloroform/water mixture. The active component separates into the aqueous phase. The resulting aqueous extract is then reextracted with a mixture of a more polar solvent and water, such as ethylacetate/water, with the active components separating into the ethylacetate phase. The aqueous phase can then be reextracted with an even more polar solvent/water mixture, such as n-butanol/water to recover additional active components.

The active components in the ethylacetate extract can be purified by affinity or molecular weight chromatography. In a preferred embodiment, the active components in the ethylacetate extract is further purified by chromatography on a silica gel open column, an octyldecyl-reverse phase open column, and HPLC, to yield more purified fractions. As shown in FIG. 2, the ethylacetate extract applied to a silica gel column is eluted using a gradient of 0% to 20% methanol; the active component is eluted at 10% methanol. This isolate can be further purified by chromatography on a C18 reverse phase open column eluted with a gradient of 25 to 45% acetonitrile, with the active component eluting at 30% acetonitrile. When further purified by HPLC, using a 0 to 40% acetonitrile gradient, the active component elutes at between approximately 10 and 20% acetonitrile.

Further purification can be achieved using standard methods known in the art such as chromatography.

(4) Pharmaceutically Effective Compositions.

Pharmaceutical compositions containing shanzha, for administration to a patient in an amount effective to decrease blood lipids, can be prepared alone or in combination with appropriate pharmaceutical stabilization compounds, delivery vehicles, carriers, and/or other additives according to methods well known in the art. Unless otherwise defined the term "shanzha" as used herein includes shanzha extracts, concentrates, and purified components. In the preferred embodiment a crude active extract or partially purified active extract prepared, for example, as illustrated in FIG. 1 or 2, respectively, is administered orally. Methods for combining the extracts with pharmaceutical compounds are well known in the art.

The concentration of shanzha in the pharmaceutical composition will depend on absorption, inactivation, and excretion rates of the drug as well as other factors known to those of skill in the art, and will be an amount effective to decrease blood lipids. Blood lipid levels are assayed by standard techniques.

The shanzha can be incorporated with exctpients and used, for example, in the form of powders, pills, tablets, troches, or capsules. Pharmaceutically compatible binding agents, and/or adjuvant materials can be included as part of the composition. The powders, tablets, pills, capsules, troches, or the like can contain any of the following ingredients, or compounds of a similar nature: a binder such as microcrystalline cellulose, gum tragacanth, or gelatin; an excipient such as starch or lactose; a disintegrating agent such as alginic acid, Primogel™, or corn starch; a lubricant such as magnesium stearate or sterotes; a glidant such as colloidal silicon dioxide; a sweetening agent such as sucrose or saccharin; and/or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or other enteric agents.

The shanzha can be contained as a component of a fluid such as an elixir, suspension, beverage, liquid dietary supplement or substitute, or syrup; or of a solid such as a wafer, candy, chewing gum, or the like. Any of these compositions may contain, in addition to the active compounds, other components, for example, sweetening agents such as sucrose or artificial sweeteners; consumable fluids such as water, fruit juices, or vegetable juices; stabilization compounds; texturizers; nutritional enhancers such as dietary supplements, vitamins, minerals, and fiber; and certain preservatives, dyes and colorings, and flavors. Shanzha or the active extracts thereof can also be mixed with other active materials that do not impair the desired action, or with materials that supplement the desired action, such as other lipid-lowering pharmaceutical compositions.

In one preferred embodiment, shanzha or an active extract thereof is prepared with carriers that will protect the compound against rapid elimination from the body, such as a controlled release formulation, including microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can be obtained commercially.

Liposomal suspensions are also pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an organic solvent that is then evaporated, leaving behind a thin film of dried lipid on the surface of the container. An aqueous solution of the shanzha is then introduced into the container. The container is then swirled by hand to free lipid material from the sides of the container and to disperse lipid aggregates, thereby forming the liposomal suspension.

Pharmaceutical compositions containing shanzha must be stable under the conditions of manufacture and storage and may be preserved against the contaminating action of microorganisms, such as bacteria and fungi, through the use of antioxidants such as Vitamin E and ethoxyquin and bacteriostatic agents, which are on the list of compounds approved for use by the Food and Drug Administration.

In the most preferred embodiment, the shanzha is combined with a carrier for oral administration as a powder or tablet, alone or in combination with other foods, or with consumable liquids, consumable liquids to form a beverage. Consumable liquids include, for example, water or other fruit or vegetable juices. Preservatives, sweeteners, stabilization compounds, color additives, texturizers, flavor additives or enhancers, and/or nutritional enhancers such as dietary supplements, vitamins, minerals, and fiber can also be added.

Methods of Treating Hyperlipidemias, Hyperlipoproteinemias, Hypercholesterolemias, and Disease States Associated with each.

Shanzha can be used for the treatment of hyperlipidemias, including hypercholesterolemia; hyperlipoproteinemia, including high serum levels of LDL and IDL; and disease states associated with each, such as atherosclerosis and pancreatitis. Shanzha can also be used in normal subjects as a preventative measure to prevent the occurrence of these disorders. Mammals, and specifically humans, suffering from any of these disorders or wishing to prevent any of these disorders can be treated by administering to the patient, in an amount effective to decrease blood lipids, a pharmaceutical composition containing shanzha.

In a preferred embodiment, shanzha in an amount effective to decrease blood lipids, alone or in combination with stabilizers, delivery vehicles, carriers, and the like, is administered to patients in need of treatment thereof, most preferably by oral administration. The amount effective to decrease blood lipids is normally an amount that will maintain serum cholesterol levels in a range of about 160 to 200 mg/dl in humans, as assayed by standard blood lipid assays.

Typical systemic dosages of shanzha as prepared according to the methods illustrated in FIG. 1 or 2, are those in a preferred dosage range equivalent to about 10 to 50 gm of crude extract per day for a 60 kg human. Preferably the composition is administered as a single daily dose or divided daily doses, most preferably three doses given before, during, or after meals. Patients can be maintained on shanzha indefinitely to achieve and maintain low serum cholesterol levels of between 160 and 200 mg/dl.

Conditions to be considered in selecting dosage level, frequency, and duration primarily include the severity of the patient's disorder, the patient's serum cholesterol level, adverse side effects such as gastric distress, and the patient's need for preventive therapy, as well as the therapeutic efficacy. It is believed that shanzha or active extracts thereof can be taken at will, with appropriate monitoring for side effects. It is to be understood that for any particular subject, specific dosage regimens should be adjusted over time according to the individual patient need and the professional judgment of the person administering or supervising the administration of the compositions, and that the concentration ranges set forth herein are exemplary only and are not intended to limit the scope or practice of the claimed composition. Other concentration ranges and dosage durations can be determined by routine experimentation.

It is to be further understood that although the preferred route of administration is by oral administration of the shanzha or active extracts thereof, other forms of administration can be used.

Preferably, shanzha or active extracts thereof, in an amount effective to decrease blood lipids, is contained in a fruit juice or water based beverage, powder form sprinkled over or incorporated into food to be consumed as part of the normal daily diet, is administered as a pill, pellet, tablet, or capsule which is administered to the patient in need thereof before, during, or after meals.

Assays for Determining Activity of Shanzha or Active Extracts Thereof.

In a simple embodiment, eucaryotic cells having functional LDL receptors naturally occurring on their surface and having the ability to internalize and process the bound LDL in a way that results in up- or down-regulation of the receptors, preferably mammalian cells and preferably HepG2 cells, are used in standard binding assays, such as competitive binding assays, in which the ligand, preferably LDL, is used in labeled states, such as labeled with a radio-label fluorescent label, dye, or chemiluminescent compound, or unlabeled states, to test for the activity of compositions derived from shanzha or active extracts thereof in inhibiting the down-regulation of the LDL receptors, enhancing the up-regulation of such receptors, or lowering serum lipids such as cholesterol or LDL.

In another assay, shanzha or active extracts thereof can be tested in eucaryotic cells expressing functional LDL receptors on their surface, preferably mammalian cells and preferably HepG2 cells, for their activities in modulating the binding of proteins extracted from mammalian cells to specific elements of the LDL receptor genes, including its promoter region. Mammalian cells, preferably HepG2 cells, expressing functional LDL receptors on their surfaces, are grown in cell culture under standard conditions in the presence or absence of known concentrations of various extracts of shanzha and LDL. Cells are then dissolved and fractionated. Selected fractions, preferably a nuclear protein fraction, are incubated with labeled elements of the LDL receptor gene or corresponding synthetic nucleotide sequences thereof, preferably the nucleotide sequence encoding the Repeat 2 sequence of the promoter region, and then assayed for binding activity by standard techniques known in the art. Comparisons in the amount of specific and non-specific bound and unbound protein, compared to controls, are used to determine which extracts are effective in modulating the LDL receptor gene.

The methods for treating hyperlipidemia, including, for example, hyperlipoproteinemia and hypercholesterolemia, and associated disease states by administering shanzha or an active extract thereof, and for assays to determine which extracts of shanzha are effective for such treatment, will be more fully understood by reference to the non-limiting examples described below.

General Description of Methods.

Cell Culture.

Human hepatocellular carcinoma (HepG2) cells (obtained from the American Type Culture Collection, Rockville, Md., catalog number HB8065) were grown at 37° C. in 5% $CO_2$ in air for 48 hours before experimental procedures were begun, in a basic medium consisting of RPMI1640 medium buffered with 20 mM Hepes salt, pH 7.4, and supplemented with 10% fetal bovine serum, 100 U/ml penicillin, 100 μg/ml streptomycin, and 2.5 μg/ml fungizone (all from Gibco BRL, Life Technologies, Inc., Gaithersburg, Md.).

Receptor Binding Assay.

Low density lipoprotein (LDL) and lipoprotein deficient serum (LPDS) were prepared by sequential ultracentrifugation in different densities as follows. Fresh pooled sera obtained from donors were centrifuged in a model L5 Beckman ultracentrifuge (Beckman Instruments, Palo Alto, Calif.) at 40,000 rpm at 10° C. for 18 hours using a Beckman 42.0 angle rotor. The very low density lipoprotein (VLDL) fraction (top ⅓) was removed. The density of the remaining fraction was adjusted to 1.063 gm/ml by addition of a sodium bromide solution of 1.1816 gm/ml density in a ratio of 1:2. The mixture was then centrifuged as before for 24 hours. The LDL fraction (top ⅓) was removed and dialyzed extensively against 0.01M phosphate buffered saline, Ph 7.4, and filter sterilized by passage through a 0.2 μm filter. This preparation was used as LDL in all cell culture experiments.

After removal of the LDL fraction, the remaining fraction (bottom ⅔) of the centrifuged serum was adjusted to a density of 1.21 gm/ml by addition of a sodium bromide solution (density 1.474 gm/ml) in a ratio of 1:2, and then centrifuged as before for 48 hours. The high density lipoprotein (HDL) fraction (top ⅓) was removed, and the remaining fraction (bottom ⅔), free of any serum lipoprotein, was dialyzed extensively against 0.01M phosphate buffered saline, pH 7.4, and then sterilized by filtration. This fraction was used as LPDS in the cell culture experiments.

HepG2 cells grown in 24 well plates in RPMI medium were washed three times with phosphate buffered saline (PBS) after drug treatment. $^{125}$I-LDL was then added to a final concentration of 10 μg/ml (approximately 1 to $2 \times 10^6$ cpm) in 1 ml RPMI with 5 to 10% LPDS. Cells were incubated in the labeled medium at 37° C. for 3 to 5 hours, washed 3 times with PBS containing 1% bovine serum albumin (BSA), and then washed with PBS without BSA 3 times more. Cell monolayers were dissolved in 1 ml 1N of NaOH.

Total radioactivity and protein concentration were then determined as follows. An aliquot of 0.2 ml solubilized cells was used for protein determination, using the method of Lowry et al., 139 *J. Biol. Chem.* 265–275 (1951). An aliquot of 0.8 ml solubilized cells was taken for radioactive counting in an automatic gamma scintillation counter (Korntron, Milan, Italy). Total radioactivity bound and internalized by the cells was measured and is known to be a reasonable means for estimating the number of LDL receptors on the cell surface. Total bound LDL was calculated from the amount of bound radioactivity multiplied by the specific activity of the $^{125}$I-LDL preparation. Results were normalized to LDL per mg cell protein specific binding is the difference between total binding of $^{125}$I-LDL carried out in the absence or presence of 500 μg/ml cold LDL. Unless otherwise stated, all results are presented as specific binding.

Animal Experiments.

Sprague-Dawley (SD) rats (obtained from Chinese University of Hong Kong) of either sex, four to six months in age and weighing 250 to 450 gm, were maintained on a normal diet of rat chow (Ralston Purina Co., Inc., St. Louis, Mo.) for four weeks in the control groups. Rats were then made hypercholesterolemic by feeding a 2% cholesterol diet (Ralston Purina Co., Inc.) for the duration of the experiment. All animals were fed ad libitum. The rats were exposed to a 12-hour light and dark cycle.

Active shanzha extract was prepared from the shanzha fruit as illustrated in FIG. 1 and described under "Preparation of an active shanzha extract from natural sources." The resulting lyophilized powder was suspended in water at a concentration of 0.75 gm/ml and boiled in a water bath until all materials were dissolved.

EXAMPLE 1.

Hypocholesterolemic Effects of Shanzha on Rats.

To test the effect of shanzha on the serum level of cholesterol in vivo, active shanzha extract was administered to the hypercholesterolemic animals in the experimental groups orally by force feeding 2.5 ml of the solution twice a day at 9:00 A.M. and 4:30 P.M. with a stainless steel feeding tube, for a total of 3.75 gm per day. Control group animals received the high cholesterol diet but were treated with water alone.

At specific time points (one week before the start of the high cholesterol diet, at the start of the high cholesterol diet, and at weekly intervals for seven weeks after the start of the high cholesterol diet), blood was drawn from the tail vein of the animals. Total cholesterol was extracted from the serum samples by a modified chloroform/methanol procedure, as described by Sperry, W. M., and F. C. Brand, 213 *J. Biol. Chem.* 69–76 (1955), using the following basic steps. Methanol/chloroform (2.5 ml; 1:1, v/v) was added to 0.2 ml serum and vortexed for about 10 seconds. Insoluble materials were removed by centrifugation at 2000 × g for 10 minutes. The clear supernatant was transferred to a new tube and back-extracted with an equal volume of distilled water. After removal of the aqueous phase, the organic phase was dried under a gentle stream of $N_2$ at 40° C.

The cholesterol content in the samples was determined by an enzymatic procedure using a lyophilized serum as the standard, as described by Allain, C. C., et al., 20 *Clin. Chem.* 470–475 (1974), using the following steps. The dried lipid extract was suspended in 0.25 ml assay buffer (0.1M phosphate buffer, pH 6.7, 25 mM 4-aminoantipyrine, 50 mM sodium cholate, and 2.5 mM polyethylene glycol (Carbowax™ 6000). After mixing, 0.1 ml of the solution was transferred to a well in a 96 well plate and 0.1 ml of an enzyme mix in 0.1M phosphate buffer containing 140 mM phenol, 5 U/ml cholesterol oxidase, 5 U/ml cholesterol ester hydrolase, and 50 U/ml horse radish peroxidase was added. After incubation at 37° C. for 1 hour, optical density (OD) at 492 nm was read in a BioRad microtiter plate reader (Richmond, Calif.). All reagents in the assay were obtained from Sigma Chemical Co. (St. Louis, Mo.).

Figure 4:
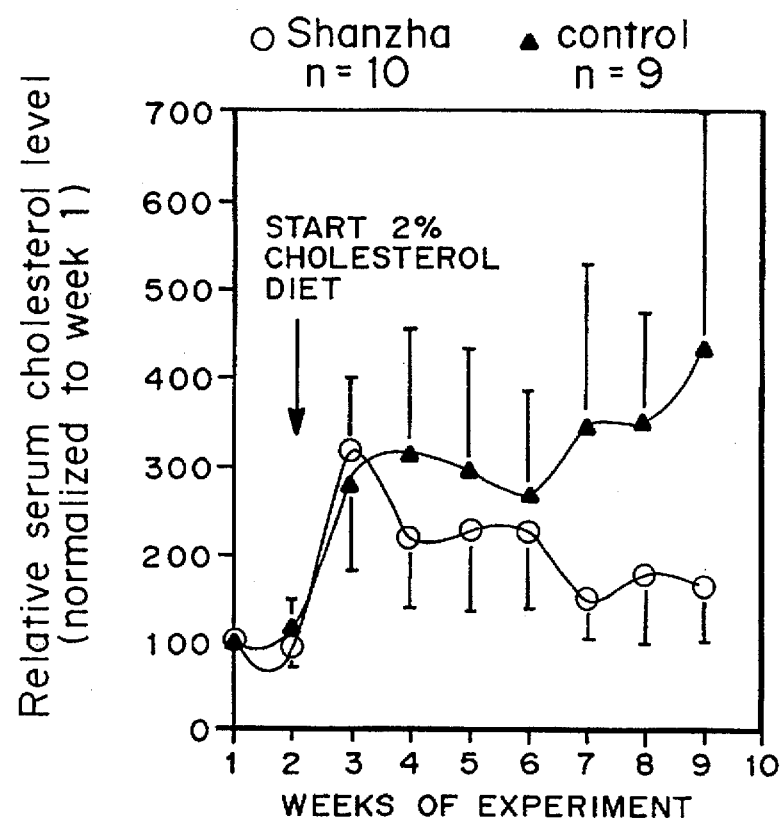
FIG. 4 is a graph illustrating the effect over time (weeks) of an orally administered crude extract of shanzha on the serum cholesterol level of rats fed a two per cent cholesterol enriched diet for up to eight weeks. The relative serum cholesterol level is normalized to week one.
Figure 5:
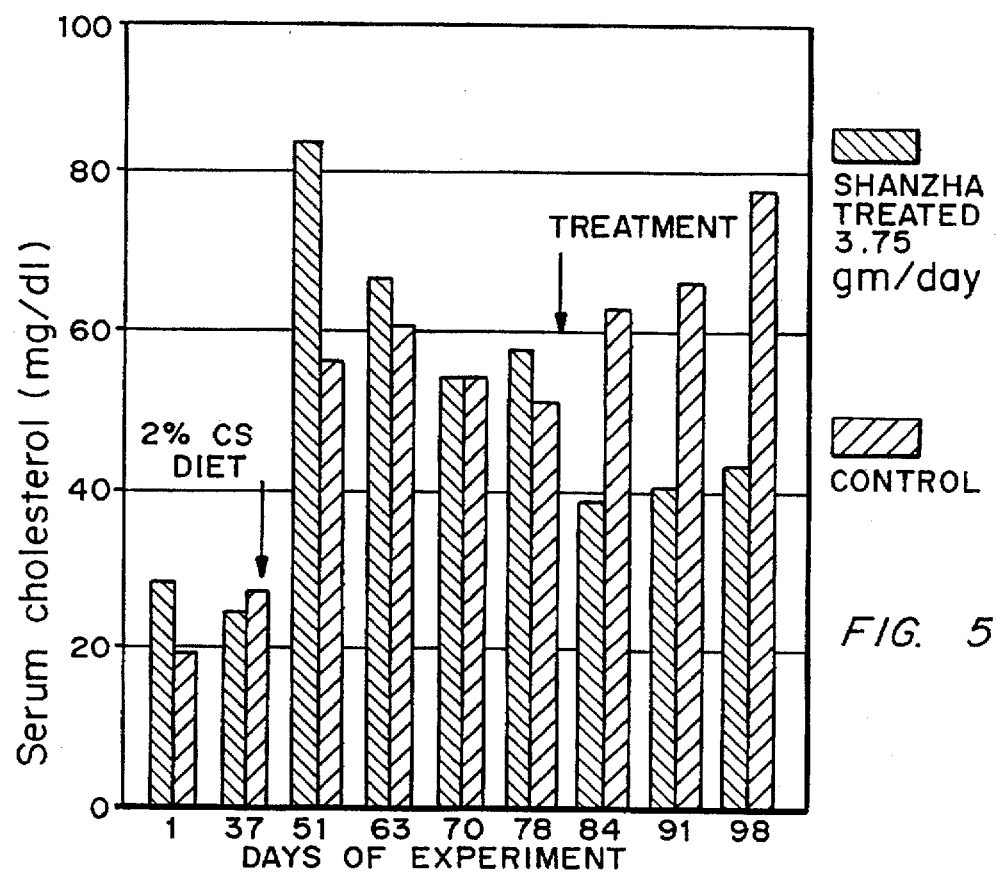
FIG. 5 is a graph showing the effects of an orally administered crude extract if shanzha (3.75 gm/day) on serum cholesterol levels (in mg/dl) in rats fed a two per cent cholesterol enriched diet over 98 days, compared to untreated control levels.

The results are shown in FIGS. 4 and 5. Oral administration of shanzha extract significantly suppressed the increase in the level of serum cholesterol in experimental animals that occurred in control animals that were maintained on the same high cholesterol diet. Compared with control animals treated with water alone, shanzha not only suppressed the increase of serum cholesterol from the cholesterol-enriched diet, but also lowered the level of serum cholesterol.

FIG. 4 shows the results in the first experiment of shanzha on the serum cholesterol of rats (ten experimental and nine control) fed the high cholesterol diet. The shanzha treated group (O—O—O) received the high cholesterol diet beginning at week two of the experiment. After about one week on the cholesterol diet, their serum cholesterol began to drop and was maintained substantially below that of untreated control rats.

FIG. 5 shows the results in the second experiment of the effects of shanzha extract on the serum cholesterol of rats (four experimental and three control) fed a high cholesterol diet for 61 days. By day 84 in the experiment (47 days on the diet), the serum cholesterol of shanzha rats was maintained at a substantially lower level than that of untreated controls.

EXAMPLE 2.

Shanzha does not Inhibit Intestinal Cholesterol Absorption.

Intestinal absorption is a major route by which cholesterol enters the blood. To assess whether shanzha lowers the serum cholesterol level in vivo by inhibiting or preventing the intestinal absorption of cholesterol, rats were given shanzha extract or test compounds known to inhibit lipid absorption by the intestinal mucosa.

Female Sprague Dawley rats weighing between 350 and 400 gm were maintained on a normal diet, as described under "Animal Experiments." Rats were anesthetized with pentobarbital (Sigma Chemical Co., St. Louis, Mo.) and then force-fed by stomach tube lyophilized shanzha extract (prepared as described under "Preparation of an active shanzha extract from natural sources"), cholestyramine (Sigma), activated charcoal (Norit™ A, Sigma), or water. Shanzha extract and the test compounds were suspended at a concentration of 0.25 gm/ml in water and administered at a dose of 1 ml. Fifteen minutes after the feeding, 0.5 ml corn oil (from local supermarket) containing 5 μCi $^3$H-cholesterol (Amersham International plc, Amersham, U.K.) was administered by the same method. At hourly intervals from one to five hours, 0.5 ml blood was drawn from the femoral vein by means of an implanted catheter pre-flushed with heparin to reduce clogging. After separation of serum from blood cells by centrifugation, cholesterol was extracted by ten volumes of isopropanol. Precipitated protein was removed by centrifugation, the organic extract was then mixed with a liquid scintillation fluid, and the radioactivity in it counted in a liquid scintillation counter (Beckman Instruments, Fullerton, Calif.) by standard methods.

Figure 6:
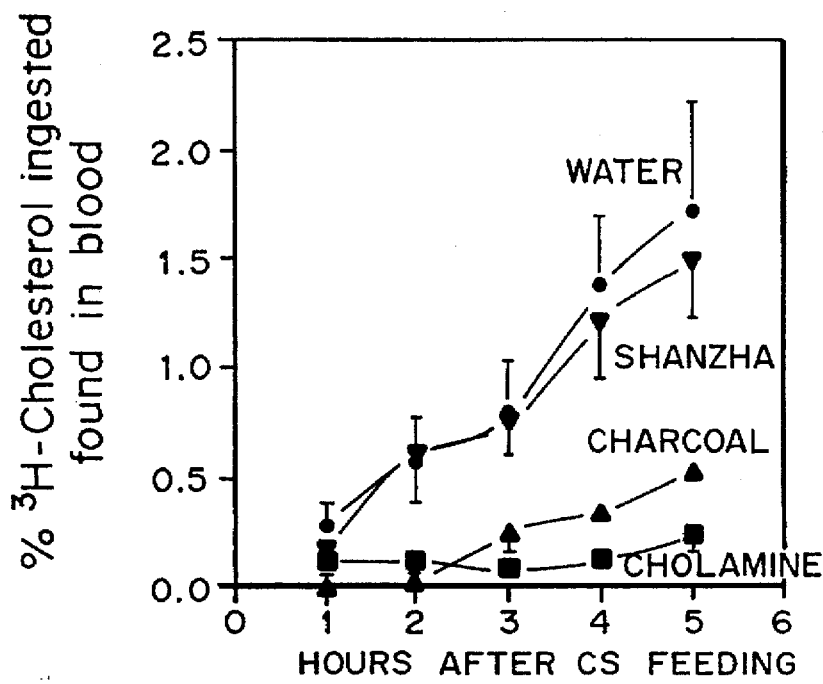
FIG. 6 is a graph depicting the comparative effects of orally administered water (circles), shanzha (inverted triangles), charcoal (triangles), and cholestyramine (squares) on blood levels of $^3$H-cholesterol in rats one to five hours after ingestion of labeled cholesterol.

The results are shown in FIG. 6. The rate of cholesterol absorption in the intestine was not affected by shanzha or water but was decreased, compared to control, by charcoal and cholestyramine. These results demonstrate that shanzha extract does not decrease serum cholesterol by inhibiting or preventing absorption of cholesterol through the intestinal mucosa.

EXAMPLE 3.

Shanzha Prevented the Down-regulation of LDL Receptor by LDL.

Ordinarily, serum cholesterol level is maintained in a steady state in which the rate of entry of cholesterol into the blood is equal to the removal of cholesterol from the blood. A lowered serum cholesterol level indicates a shift in this steady state, resulting from either a decrease in the rate of entry or an increase in the rate of removal. In the whole animal, shifts in the steady state are difficult to evaluate since the synthesis (entry) and removal of serum cholesterol are intricately balanced between the liver and other organs. However, this problem has been resolved, using a cell culture model to examine the effect of shanzha on the general mechanism of cholesterol uptake. This model was used to evaluate the effects of shanzha or active extracts thereof on two important parameters involved in serum cholesterol homeostasis: LDL receptor-mediated uptake of cholesterol from serum and de novo synthesis of cholesterol by cells.

The effects of shanzha on LDL receptor level were investigated in HepG2 cells as follows.

HepG2 cells were maintained as described above under "Cell Culture." The cells were incubated in media that were supplemented with human LPDS with or without added LDL, both prepared according to the methods described under "Receptor Binding Assay," at concentrations of 0, 50, 100, 150, or 200 μg LDL/ml medium, in the presence or absence of shanzha extract (prepared according to the method shown in FIG. 1 and described under "Preparation of an active shanzha extract from natural sources") added to the medium at 1.0 mg/ml. At the end of the incubation period, shanzha extract and LDL were removed by washing with PBS, and LDL receptor binding activity was determined by binding with $^{125}$I-labeled LDL, as described under "Receptor Binding Assay."

Figure 7:
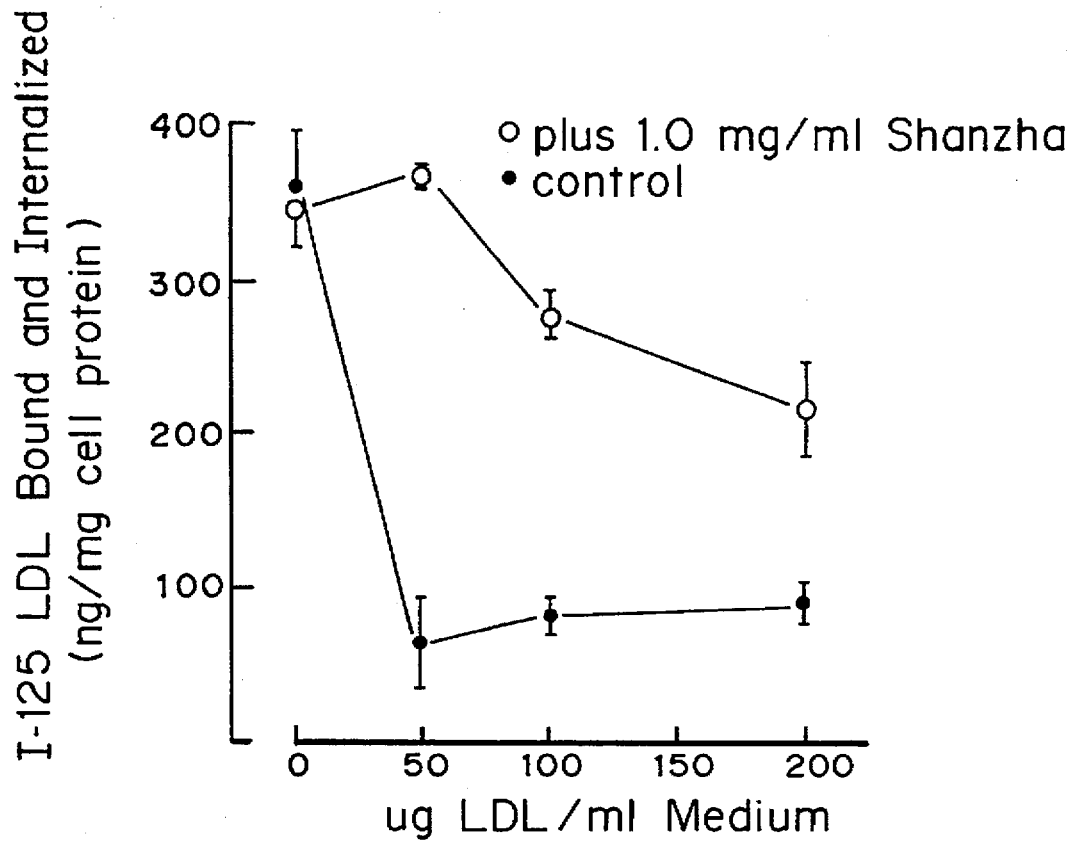
FIG. 7 is a graph illustrating the effects of administration of a Crude extract of shanzha (1.0 mg/ml medium) on the amount of $^{125}$I-labeled low density lipoprotein (LDL) (expressed in ng/mg cell protein) bound and internalized in cultured HepG2 cells incubated in increasing concentrations of LDL (0, 50, 100, and 200 µg LDL/ml medium), compared to untreated controls.

As shown in FIG. 7, in the absence of shanzha, the LDL receptor was down-regulated by increasing intracellular concentrations of the LDL ligand. However, down-regulation of the LDL receptor was significantly suppressed in the presence of shanzha.

Figure 8:
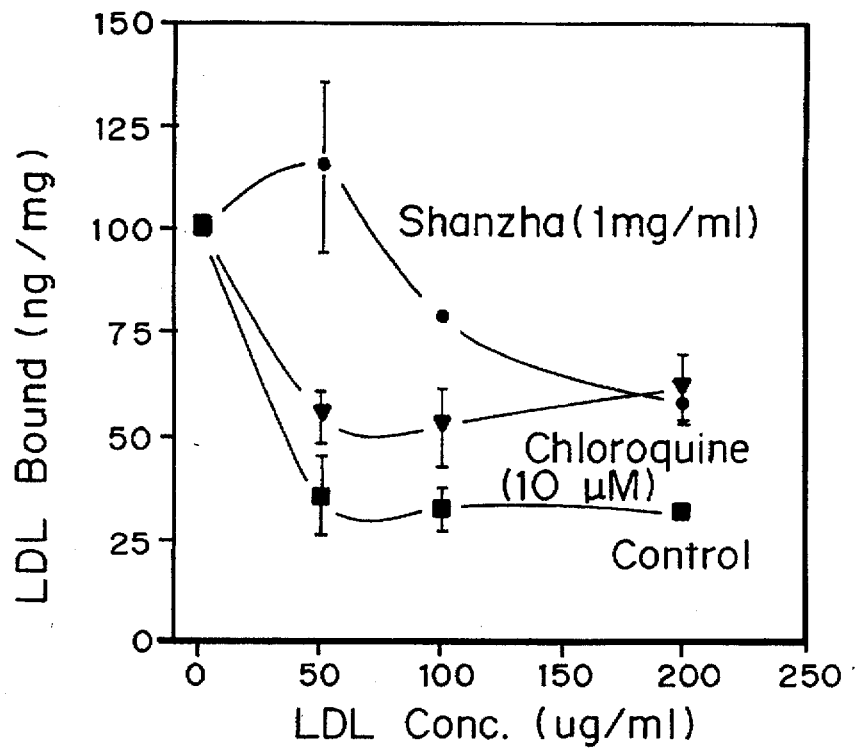
FIG. 8 is a graph showing the effects of shanzha (circles) (1 mg/ml medium) and chloroquine (inverted trianges) (10 µM) treatment on the levels of LDL (ng/mg cell protein) bound by cultured HepG2 cells incubated in increasing concentrations of LDL (0, 50, 100, and 200 µg/ml medium), compared to untreated controls (squares).

The effect of shanzha on inhibition of down-regulation of the LDL receptor was compared with the effect of chloroquine, a well known inhibitor of LDL receptor down-regulation. HepG2 cells were incubated as described above in increasing concentrations of LDL in the presence of shanzha (1 mg/ml medium) or chloroquine (10 µM in medium) (Sigma). The results are illustrated in FIG. 8, which shows that shanzha was more effective in inhibiting the down-regulation of LDL than chloroquine.

EXAMPLE 4.

Dose Effects of Shanzha.

The dose effect of different concentrations of the crude shanzha extract, prepared as described under "Preparation of an active shanzha extract from natural sources" and shown in FIG. 1, on the binding of LDL by LDL receptors was ascertained as follows.

HepG2 cells, grown and maintained as described under "Cell Culture," were incubated in media containing increasing concentrations of the shanzha extract (0.0, 0.5, and 1.0 mg/ml medium) in the presence and absence of LDL (200 µg/ml medium). Receptor binding activities were determined after 48 hours of incubation, as described above in "Receptor Binding Assay."

Figure 9:
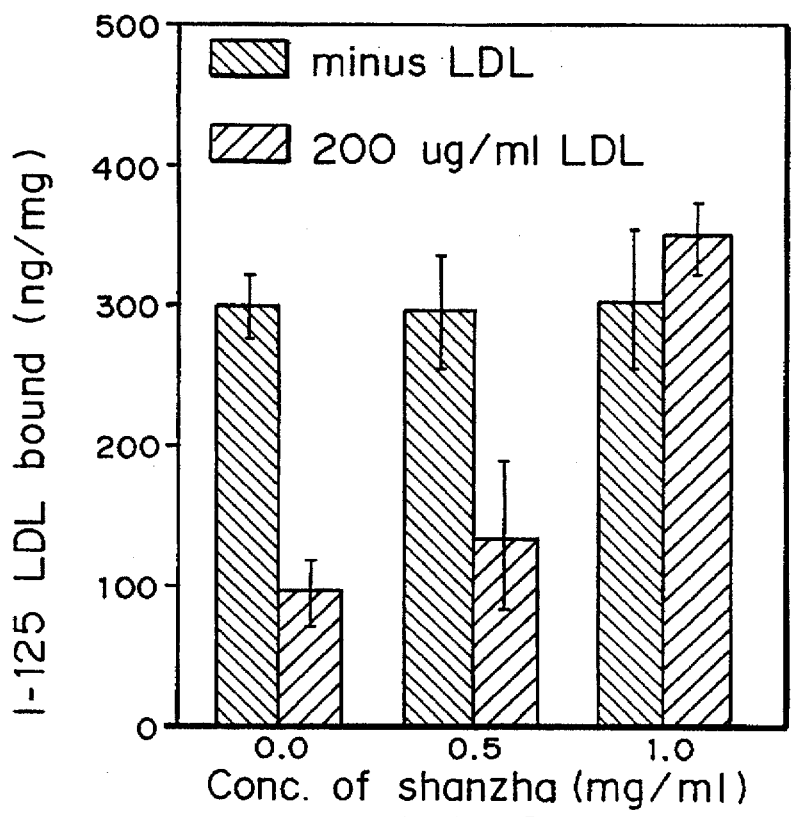
FIG. 9 is a dose response graph depicting the effects of increasing concentrations of a crude extract of shanzha (0.0, 0.5, and 1.0 mg/ml medium) on the levels of $^{125}$I-LDL (ng/mg cell protein) bound by cultured HepG2 cells incubated in media with and without 200 µg/ml LDL in the media.

As shown in FIG. 9, in the absence of LDL no change in receptor level was apparent when cells were incubated in media containing either 0.5 or 1.0 mg/ml of the shanzha extract. In contrast, in media containing 200 µg/ml LDL, receptor binding of LDL was significantly increased at 1.0 mg/ml but not at 0.5 mg/ml shanzha extract.

The effect of the crude extract of shanzha in the up-regulation of the LDL receptor appears to be variable from batch to batch. The results from a similar experiment show that although this batch of shanzha extract up-regulated the LDL receptor, its net potency in promoting binding compared with the zero control was significantly lower (1.5 compared to the 3.7 times increase shown in FIG. 9).

EXAMPLE 5.

Action of Shanzha Compared to Lovastatin.

Lovastatin is known to be a potent inhibitor of HMGCoA reductase, a key enzyme in cholesterol biosynthesis by cells. Lovastatin lowers serum cholesterol by inhibiting de novo cholesterol synthesis and concomitantly increasing the number of LDL receptors in liver. To evaluate whether the mechanism of action of shanzha or active extracts thereof is different from that of lovastatin, binding studies were performed with these compounds using HepG2 cells incubated in increasing concentrations of LDL (0, 50, and 200 µg/ml medium). LDL receptor binding activity was assayed as described under cells users grown and "Receptor Binding Assay." HepG2 cells were grown and maintained as described under "Cell Culture." An active extract of shanzha was prepared according to the method described under "Preparation of an active shanzha extract from natural sources" and shown in FIG. 1.

Figure 10:
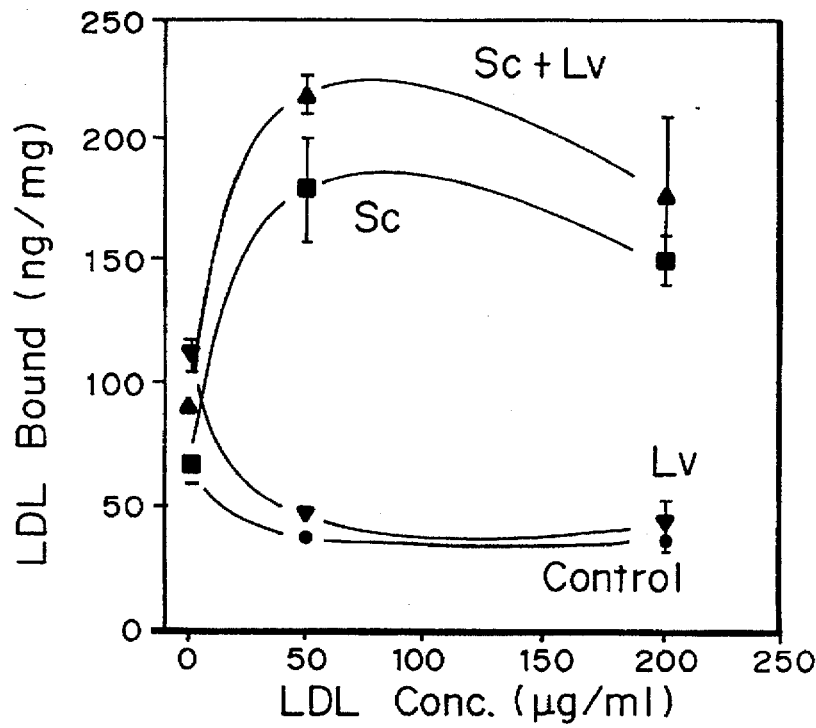
FIG. 10 is a graph in which the effects of shanzha (Sc, squares) treatment alone, combined shanzha and lovastatin treatment (Sc+Lv, triangles), lovastatin treatment alone (Lv, inverted triangles), and no treatment (control, circles) on the levels of LDL (ng/mg cell protein) bound by cultured HepG2 cells incubated in increasing concentrations of LDL (0 to 200 µg/ml medium) are compared.
Figure 11:
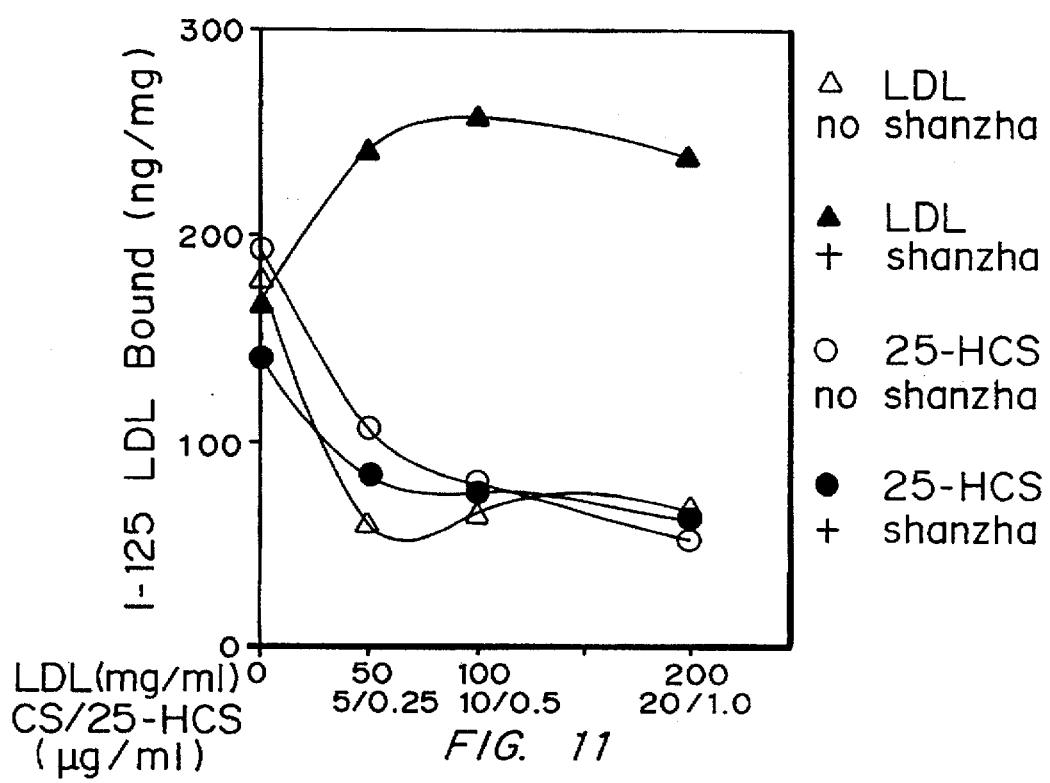
FIG. 11 is a graph in which the effects of LDL treatment alone, LDL plus shanzha treatment, 25-hydroxycholesterol treatment alone, and combined shanzha and 25-hydroxycholesterol treatment on the levels of $^{125}$I-LDL (ng/mg cell protein) bound by cultured HepG2 cells incubated in increasing concentrations of LDL (0 to 200 µg/ml medium) and cholesterol/25-hydroxycholesterol (0 to 20/1.0 µg/ml) are compared.

FIG. 10 demonstrates that pretreatment of HepG2 cells with 0.4 µg/ml lovastatin (Merck, Sharp & Dohme Research Laboratories, Merck & Co., Inc., Rahway, N.J.) for 48 hours increased LDL receptor binding activity by 50 per cent when LDL was absent from the incubation medium. However, this increase became insignificant in the presence of 50 and 200 µmg/ml LDL. These results were expected since internalization of LDL would supply enough cholesterol to suppress receptor synthesis and down-regulate the LDL receptor. As observed in Example 3 and in this experiment, treatment with 1 mg/ml crude shanzha extract significantly up-regulated the LDL receptor in the presence of LDL. This result is opposite the result of treatment with lovastatin.

Moreover, as shown in FIG. 14 (bar 7), high levels of intracellular cholesterol induced by shanzha apparently had no effect on the down-regulation of the receptor demonstrated in FIG. 10. When cells were pretreated with shanzha and lovastatin together, the induction of LDL receptor level, i.e., the up-regulation of the LDL receptor, was higher than when cells were pretreated with shanzha alone. These data demonstrate that lovastatin and shanzha have different modes of action.

EXAMPLE 6.

Shanzha Did Not Prevent Down Regulation of LDL Receptor by 25-Hydroxycholesterol Cells can take up 25-hydroxycholesterol using a non-LDL-receptor mediated mechanism. Once the 25-hydroxycholesterol enters the cells, it can induce the same metabolic events as LDL-cholesterol, including the down-regulation of the LDL receptor and the turning off of cholesterol synthesis involving HMGCoA reductase. Since shanzha was shown to inhibit the down-regulation of LDL receptor by LDL, the ability of shanzha or active extracts thereof to distinguish cholesterol taken up by the LDL receptor from cholesterols that are not taken up by the LDL receptor was assessed.

HepG2 cells were grown and maintained as described under "Cell Culture." An active extract of shanzha was prepared according to the method described under "Preparation of an active shanzha extract from natural sources" and shown in FIG. 1. Cells were incubated for 48 hours in media containing increasing concentrations of LDL (0, 50, 100, and 200 µg/ml medium) alone; increasing concentrations of LDL (0, 50, 100, and 200 µg/ml medium) plus shanzha (1 mg/ml); increasing concentrations of cholesterol plus 25-hydroxycholesterol (Sigma Chemical Co., St. Louis, Mo.) (5/0.25, 10/0.5, and 20/1.0 µg/ml); or increasing concentrations of cholesterol plus 25-hydroxycholesterol (same concentrations as above) plus shanzha (1 mg/ml). Receptor binding activity was then determined according to the method described under "Receptor Binding Assay," using $^{125}$I-labeled LDL.

At the concentrations of cholesterol/25-hydroxycholesterol that were tested, the activity of shanzha in up-regulating the receptor was not apparent. The mechanism by which the cells distinguished between cholesterol derived from LDL and cholesterol derived from 25-hydroxycholesterol is not known at this time. It is believed that the mechanism of down-regulation mediated by LDL is sensitive to shanzha or active extracts thereof, while that of 25-hydroxycholesterol is not.

EXAMPLE 7.

Shanzha Inhibited the Expression of a Sterol Responsive DNA Binding Protein.

The down-regulation of the LDL receptor is believed to be mediated by Repeat 2, element in the promoter region of the LDL receptor gene, through its interactions with nuclear binding proteins, which are sterol responsive. Sudhoff, T. C., et al. 262 *J. Biol. Chem.* 10773–10779 (1987). A model system was developed to test the ability of shanzha or active extracts thereof to inhibit sterol responsive gene transcription in cells or animals. The effect of shanzha on the ability of a Repeat 2 oligomer to bind to specific nuclear proteins from HepG2 cells, using a gel shift assay as described by Hennighausen, L., and H. Lubon, 152 *Meth. Enzymol.* 721–735 (1987) was measured.

For this assay, a nuclear protein fraction was prepared from HepG2 cells. HepG2 cells in log phase were harvested and washed two times with Dulbecco's phosphate-buffered saline (without calcium and magnesium) (Gibco BRL, Life Technologies, Inc., Gaithersburg, Md.). Cells were then suspended in 5 pellet volumes of 0.3M sucrose in buffer A (10 mM Hepes-KOH, pH 7.9; 10 mM KCl; 1.5 mM $MgCl_2$; 0.1 mM EGTA; 0.5 mM dithiothreitol (DTT); 0.5 mM phenylmethylsulfonyl fluoride (PMSF); 2 µg/ml bacitracin) (all from Sigma Chemical Co., St. Louis, Mo.). Cells were lysed by 8 to 12 strokes in a glass homogenizer and 1 to 2 strokes in the presence of 0.3 to 0.4% of a nonionic detergent, Nonidet P-40™ (Sigma). The homogenate was then centrifuged at 1200×g for 10 minutes, and the pelleted nuclei were washed twice in 0.3M sucrose in buffer A without Nonidet P-40™. The nuclei pellet was then suspended with a glass homogenizer in 2.5 pellet volumes of 400 mM EGTA, 0.5 mM DTT, 5% glycerol and 0.5 mM PMSF (all from Sigma). The suspended nuclei were stirred slowly for 30 minutes at 4° C. and then centrifuged for 60 minutes at 100,000 × g. The supernatant was dialyzed against 50 volumes of 20 mM Hepes-KOH at pH 7.9, 75 mM NaCl, 0.1 mM EDTA, 0.5 mM DTT, 20% glycerol and 0.5 mM PMSF (all from Sigma). After dialysis, any insoluble materials were removed by centrifugation at 25,000 × g for 15 minutes. This nuclear protein extract was then divided into small portions and stored at −70° C. for DNA binding analysis.

A 16-base synthetic double-stranded oligonucleotide having the DNA sequence of Repeat 2 (SEQ ID NO:1) was prepared using routine in vitro DNA synthetic methods, as reviewed in Itakura, K., "Synthesis and Use of Synthetic Oligonucleotides," 53 *Ann. Rev. Biochem.* 323–356 (1984). The synthetic Repeat 2 oligonucleotide was $^{32}$P-labeled by standard methods known in the art using $T_4$ kinase and gamma-$^{32}$P-ATP as substrate.

For DNA binding, 1 µg of the nuclear protein was incubated with 1 ng of the $^{32}$P-labeled Repeat 2 in a 25 µl volume of a buffer composed of 10 mM Tris HCl™ (pH 7.5), 100 mM KCl, 5 mM $MgCl_2$, 1 mM DTT, 1 mM EDTA, 12.5% glycerol, 0.1% Triton X-100™ (all from Sigma), and 1 µg/ml poly(dI-dC) (Pharmacia LKB Biotechnology, Uppsala, Sweden) for 30 minutes at room temperature.

To assay for the presence of DNA binding protein in the nuclear protein fraction, 25 µl of the incubation mix was mixed with 5 µl of sample buffer (250 mM Tris HCl™, pH 8.0; 50% glycerol; 0.25% sodium azide; 0.25 mg/ml bromophenol blue; all from Sigma). Then 4 µl of this mixture was applied onto a precast 20% polyacrylamide gel (PhastGel™Homogenous 20, Pharmacia). Nuclear protein-bound Repeat 2 was separated from free Repeat 2 by electrophoresis in a PhastGel™ System (Pharmacia). Radioactivity present in the gel was visualized by autoradiography.

In this assay, the presence of a retarded band compared with oligonucleotide alone indicates the presence of a DNA binding protein. Bands that can be displaced by excess poly(dI-dC), 1 µg/ml, are considered to be non-specific for Repeat 2.

Two bands were identified that bound to $^{32}$P-Repeat 2, one specific for Repeat 2 that could not be displaced by 1 µg/ml of poly(dI-dC) and the other nonspecific for Repeat 2 that could be displaced by poly(dI-dC). This system was used to monitor the effect of shanzha or active extracts thereof on the nuclear binding proteins from HepG2 cells.

HepG2 cells were cultured in LPDS medium with the following supplements: no supplements; 1 mg/ml shanzha; 200 µg/ml LDL; 200 µg/ml LDL and 1 mg/ml shanzha extract; and 20/1.0 µg/ml cholesterol and 25-hydroxycholesterol and 1 mg/ml shanzha.

When HepG2 cells were preincubated with LDL, a significant increase in the non-specific nuclear DNA binding protein was observed. A compound that can mimic LDL in down-regulating LDL receptor, 25-hydroxycholesterol, was inactive in the induction of the non-specific binding protein. When shanzha (1 mg/ml) was included in the culture medium, the induction of the non-specific binding protein by LDL was inhibited. Shanzha treatment also resulted in an inhibition of the Repeat 2 specific protein.

Figure 15:
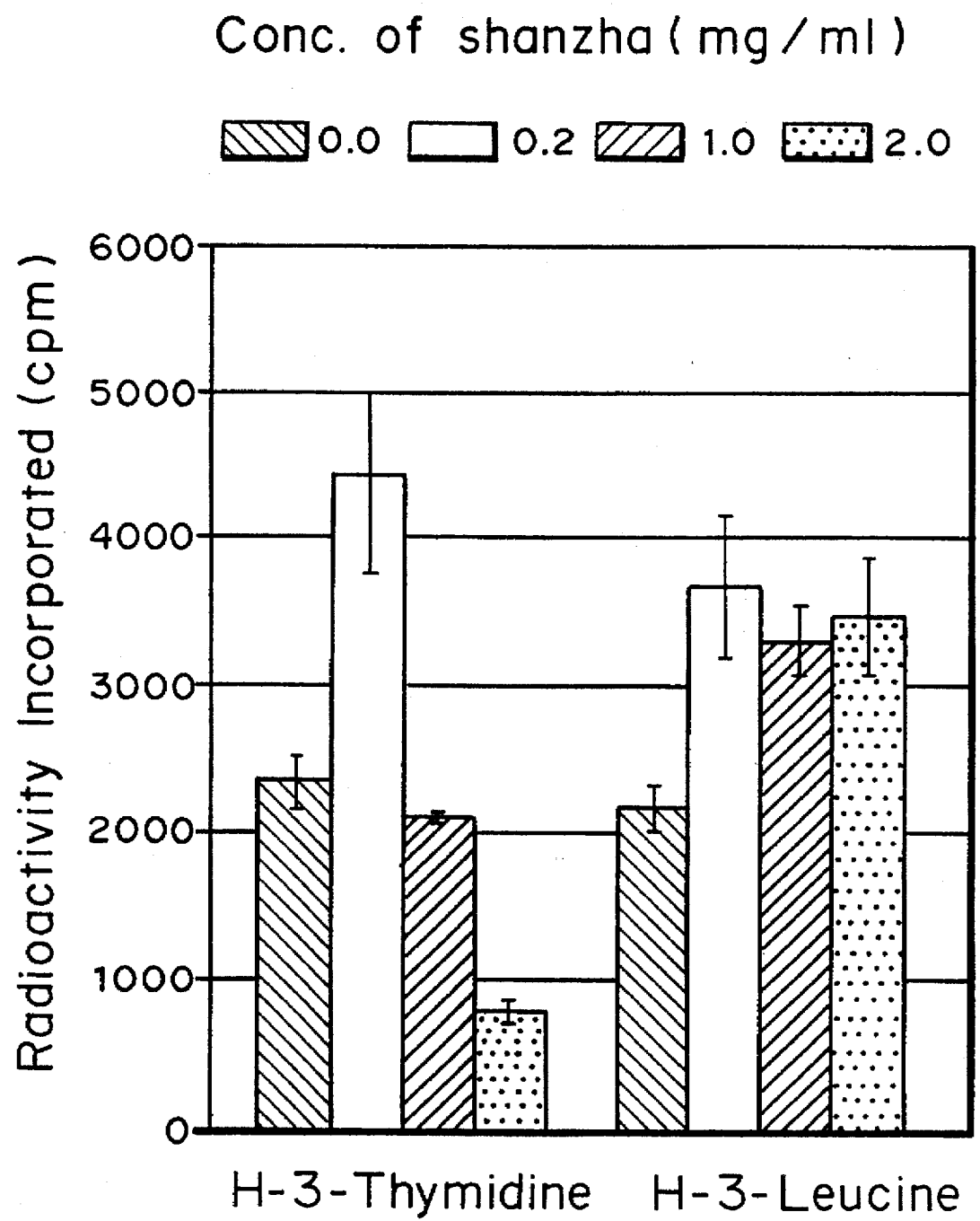
FIG. 15 is a graph in which the effects of different concentrations of shanzha (0.0, 0.2, 1.0, or 2.0 mg/ml medium) on uptake of $^3$H-thymidine or $^3$H-leucine (measured as cpm) by cultured HepG2 cells are compared.

The ability of shanzha to suppress the expression of specific and non-specific binding proteins for Repeat 2 cannot be accounted for by a non-specific inhibition of protein synthesis. Shanzha at concentrations up to 2 mg/ml had no effect in inhibiting $^3$H-leucine incorporation in HepG2 cells, as shown in FIG. 15.

EXAMPLE 8.

Up-regulation of LDL Receptor Led to an Increase in Uptake of Cholesterol.

At high intracellular levels of LDL-cholesterol, the cell normally down-regulates its receptor, which results in a decreased amount of LDL/cholesterol entering the cell. This mechanism limits the ability of the liver to clear LDL from the blood. As demonstrated in Example 3, shanzha or active extracts thereof prevented the down-regulation of the LDL receptor in hepatic cells. Cells treated with shanzha took up LDL at a higher level than non-treated cells.

To show that cells treated with shanzha or active extracts thereof are more efficient in taking up LDL from the medium, the kinetics of LDL binding and internalization were compared between cells treated with shanzha for 48 hours and untreated control cells. HepG2 cells, grown and maintained as described under "Cell Culture," were preincubated for 48 hours in standard medium supplemented with 5% LPDS and 200 µg/ml LDL, both prepared as described under "Receptor Binding Assay," with and without 1 mg/ml shanzha extract, prepared according to the method shown in FIG. 1. Cells were washed three times with phosphate buffered saline (PBS) and then incubated at 37° C. with a medium containing 5% LPDS and 10 µg/ml $^{125}$I-LDL. At 10, 30, 60, and 180 minutes, the incubation was stopped, and the cell monolayer was washed three times with cold PBS. Following this, 1 ml PBS containing 20 mg/ml dextran sulfate (Pharmacia LKB Biotechnology, Uppsala, Sweden) was added to the culture well and incubated at 4° C. for 60 minutes. The supernatant was removed and radioactivity associated with it counted in an automatic gamma counter (Kontron, Milan, Italy). The remaining cell layer was digested with 1 ml of 1N NaOH. Protein content was determined using the method of Lowry et al., 139 *J. Biol. Chem.* 265–275 (1951), and radioactivity was determined as described under "Receptor Binding Assay." The amount of LDL bound on the cell surface was calculated from the radioactivity washed off by treatment with dextran sulfate, and the amount of LDL internalized was calculated from the radioactivity remaining in the cells.

Figure 12:
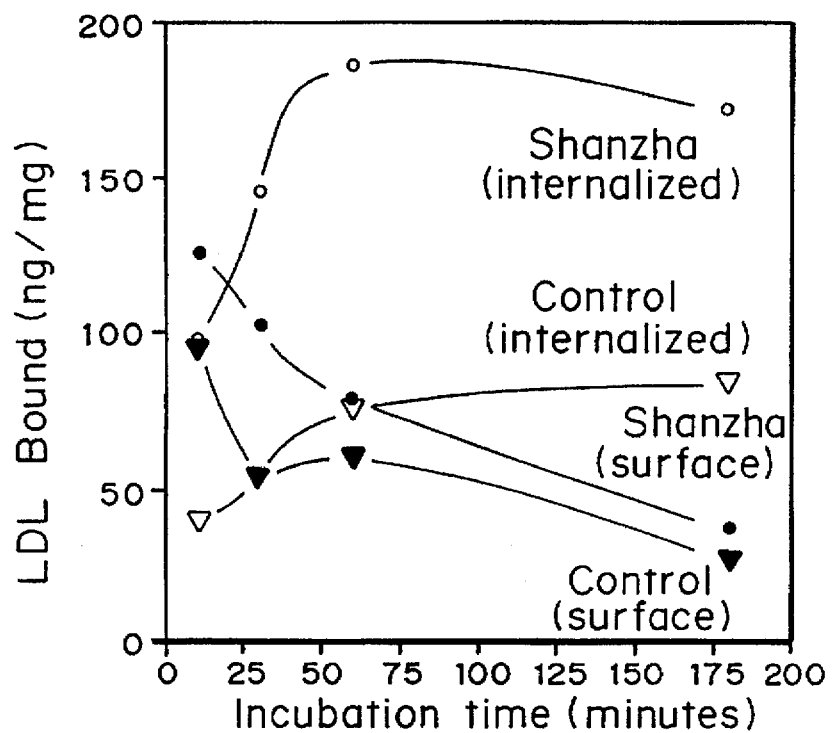
FIG. 12 is a graph illustrating the kinetics of LDL uptake, measured as LDL bound to surface (closed circles) and LDL internalized (open circles) in ng/mg cell protein, by cultured HepG2 cells in the presence and absence of shanzha over an incubation period of 180 minutes, compared to control bound to surface (closed triangles) or internalized (open triangles).

FIG. 12 shows that shanzha treatment greatly facilitated both the rate and magnitude of LDL internalization. The amount of surface bound LDL in the shanzha treated cells was also higher than in those not treated. It is believed that this facilitation of LDL uptake is related to the lipid lowering effect of shanzha in the animal experiments (FIGS. 4 and 5).

EXAMPLE 9.

Increase in Cellular Cholesterol Level by Shanzha.

Shanzha treated cells were tested to determine whether the induced increase in the number of LDL receptors is associated with an increased cholesterol content. HepG2 cells, grown and maintained as described under "Cell Culture," were pretreated with lovastatin (Merck, Sharp & Dohme, Research Laboratories, Merck & Co., Inc., Rahway, N.J.), shanzha extract (prepared as shown in FIG. 1), shanzha plus lovastatin in a lipoprotein deficient medium (LPDS, prepared according to the method described under "Receptor Binding Assay"), LDL, lovastatin plus LDL, shanzha plus LDL, or shanzha plus lovastatin plus LDL. In all samples, the concentrations of lovastatin and shanzha were 0.4 µg/ml medium and 1 mg/ml medium, respectively. LDL was added to the medium at 200 µg/ml.

Figure 13:
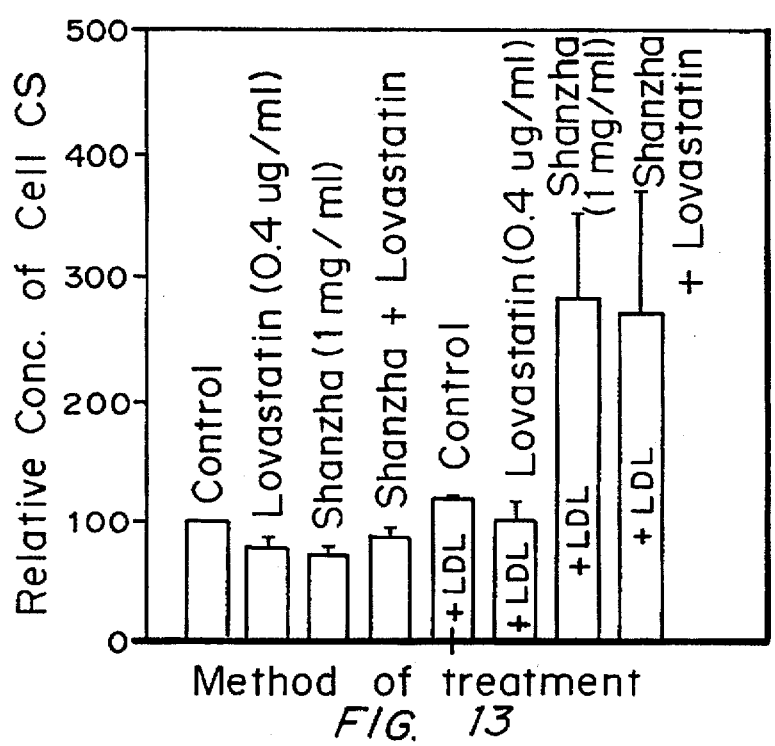
FIG. 13 is a graph illustrating the relative concentration of cholesterol in cultured HepG2 cells after treatment with lovastatin alone, shanzha alone, shanzha plus lovastatin, lovastatin alone in LDL-enhanced medium, shanzha alone in LDL-enhanced medium, or shanzha plus lovastatin in LDL-enhanced medium, as compared to untreated controls in normal or LDL-enhanced medium. The concentrations of lovastatin and shanzha were 0.4 µg/ml medium and 1 mg/ml medium, respectively.

The concentration of intracellular cholesterol was measured after 48 hours of preincubation and the results, presented in FIG. 13, were normalized relative to the control, in which the cells were preincubated without drugs or LDL. Cellular cholesterol was determined by the same technique as described in Example 1, except isopropanol was used for extraction instead of chloroform/methanol.

As shown in FIG. 10, when LDL was not present in the medium, total cellular cholesterol among the untreated, shanzha-treated, and lovastatin-treated cells was not significantly different. In the presence of LDL, cells treated with shanzha alone or with shanzha plus lovastatin (a cholesterol synthesis inhibitor) contained significantly higher levels of cholesterol. These results correspond to the data in EXAMPLES 3, 4, 5, and 8, showing that shanzha treatment increases the level of LDL receptor, leading to an increase of cholesterol accumulation in the cells.

EXAMPLE 10.

Fractionation of an Active Component.

The partial purification of the active component(s) in the crude shanzha extract, prepared according to the method shown in FIG. 1, was monitored using the LDL receptor assay, previously described.

As demonstrated in FIG. 2, the dried fruit of shanzha was extracted in organic solvent/water mixtures of increasing polarity, then separated by column chromatography and HPLC. As determined by LDL binding activity, the most purified and active material obtained was in fraction K233-3. Starting with 500 g of raw material, 9.5 mg of K233-3 was obtained by purification of extracts by thin layer chromatography using silica gel developed in a solvent system of chloroform/methanol/water (80:20:1). Only one single spot was associated with this material.

The effects of shanzha extract (prepared as shown in FIG. 1) and K233-3 on LDL binding were compared to control in HepG2 cells incubated with increasing concentrations of LDL (0, 50, 100, and 200 µg/ml medium). The amount of LDL bound by treated cells treated was measured as described under "Receptor Binding Assay."

Figure 14A:
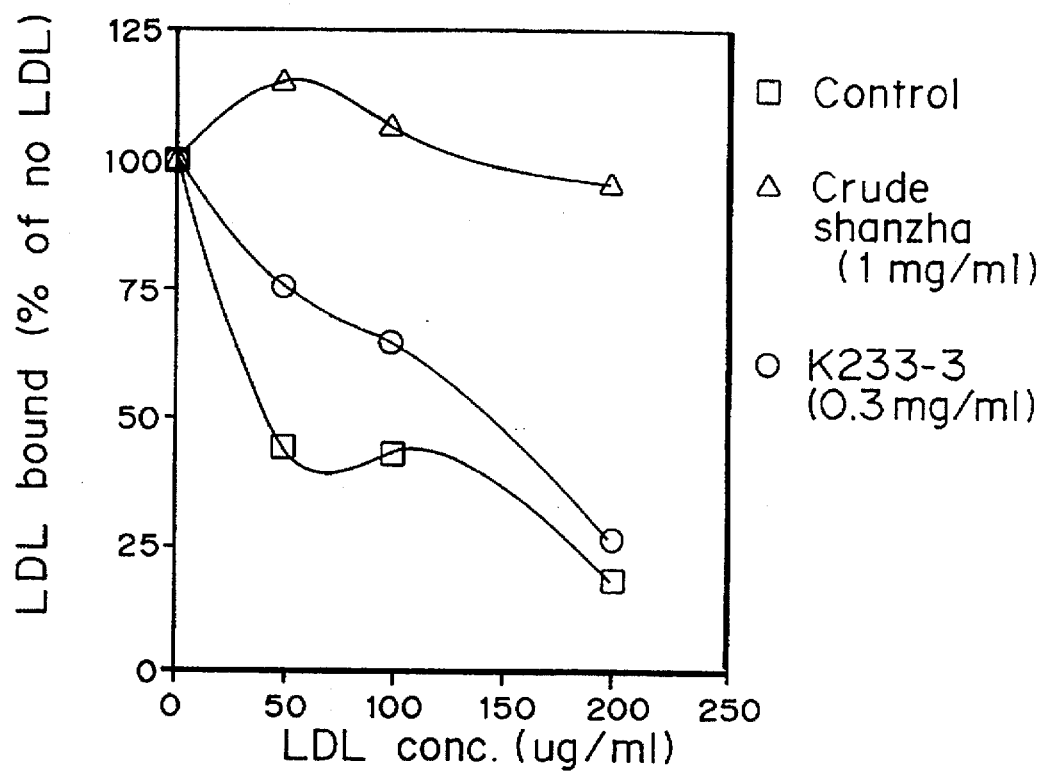
FIGS. 14a and 14b are graphs showing the effects of a crude shanzha extract (1 mg/ml, triangle) and a partially purified shanzha extract (K233-3) (0.3 mg/ml, circle) on amounts of LDL (expressed as per cent of no LDL in FIG. 14a and as ng/mg cell protein in FIG. 14b) bound by the LDL receptors of cultured HepG2 cells incubated in increasing concentrations of LDL (0, 50, 100, or 200 µg/ml medium), compared to untreated controls (square).
Figure 14B:
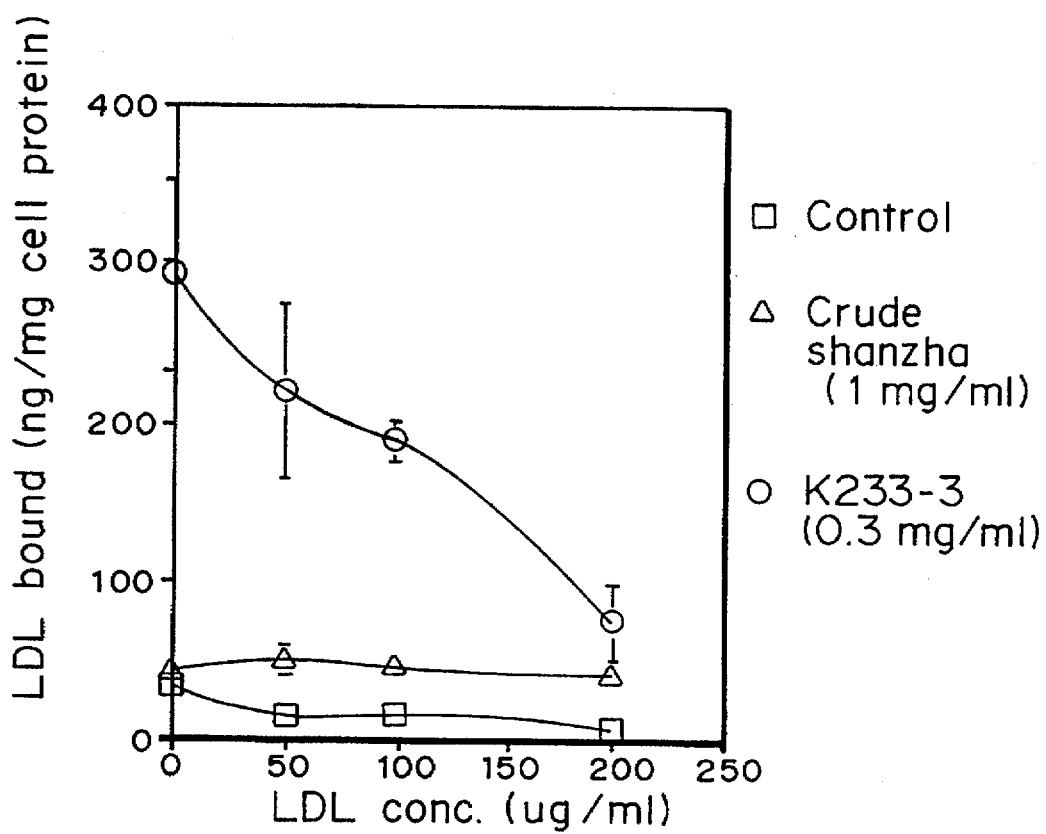

The results of the assays are shown in FIGS. 14a and 14b. Compound K233-3 (the most highly purified product obtained in this experiment) was less effective in inhibiting down-regulation than the crude shanzha extract when the data were normalized to binding at zero LDL concentration. However, as shown in FIG. 14b, the amount of LDL bound by cells treated with 0.3 mg/ml K233-3 was two to ten-fold higher than by cells treated with 1 mg/ml crude shanzha extract, depending on the level of LDL in the medium. K233-3 appears to have been more active than shanzha extract in increasing LDL receptor binding but did not prevent down regulation in these experiments. Shanzha extract can be purified further to achieve a complete activity profile, using chromatography and other standard methods known in the art.

EXAMPLE 11

Shanzha Did Not Inhibit Protein and DNA Synthesis

To determine the toxicity of shanzha or active extracts thereof, the effects of increased concentrations on the synthesis of DNA and protein were tested as follows, using $^3$H-thymidine and $^3$H-leucine incorporation, respectively, in HepG2 cells. HepG2 cells grown in a 24 well plates were incubated for 48 hours under standard culture conditions in various concentrations of shanzha extract (0.0, 0.2, 1.0, or 2.0 mg/ml medium) in a culture medium containing 5% LPDS supplemented with 200 µg/ml LDL. Three hours before the termination of the experiment, cells were labeled with either 0.5 Ci $^3$H-thymidine/ml medium (Amersham International plc, Amersham, U.K.) or 1 µCi $^3$H-leucine/ml medium (Amersham). After three hours, cells were washed three times with phosphate buffered saline and transferred to a microfuge tube. The cell pellet was then washed twice with 5% cold trichloroacetic acid (Sigma) and once with absolute ethanol. Afterwards, insoluble materials were dissolved in 1 ml of 1N NaOH. A sample (0.8 ml) was taken for liquid scintillation counting in an automatic gamma scintillation counter (Korntron, Milan, Italy), and the remaining 0.2 ml was used for protein determination by the method of Lowry et al., 139 *J. Biol. Chem.* 265-275 (1951).

The results are shown in FIG. 15. DNA synthesis was significantly stimulated by shanzha at 0.2 mg/ml medium. Only at a concentration of 2 mg/ml was $^3$H-thymidine incorporation suppressed significantly. Protein synthesis was stimulated by shanzha treatment at all dose levels. Thus, as measured by radioactivity incorporation, shanzha was not toxic to protein synthesis in cells at concentrations up to and including 2.0 mg/ml medium, and exhibited some toxicity to DNA synthesis only at concentrations of 2.0 mg/ml medium.

EXAMPLE 12

Stability of Shanzha During Storage

To determine the effects of storage on shanzha or active extracts thereof, a lyophilized powder of crude shanzha extract (prepared according to the protocol shown in FIG. 1) was stored under different conditions for up to three weeks and tested for its potency in affecting LDL receptors in HepG2 cells. Shanzha samples from the stored powder were assayed for LDL receptor binding activity as described under "Receptor Binding Assay," after storage under the following conditions:

1. Room temperature (20°–22° C.), light (room light), air (room air);
2. Room temperature, light, vacuum (vacuum desiccator with CaSO$_4$ (Drierite™, Aldrich Chemical Co., Inc., Milwaukee, Wis.));
3. Room temperature, dark (sample wrapped in aluminum foil), air;
4. Room temperature, dark, vacuum;
5. 4° C., light, air;
6. 4° C., light; vacuum;
7. 4° C., dark, air; and
8. 4° C., dark, vacuum.

The assay values were normalized to those of the initial week for easy comparison.

Figure 16:
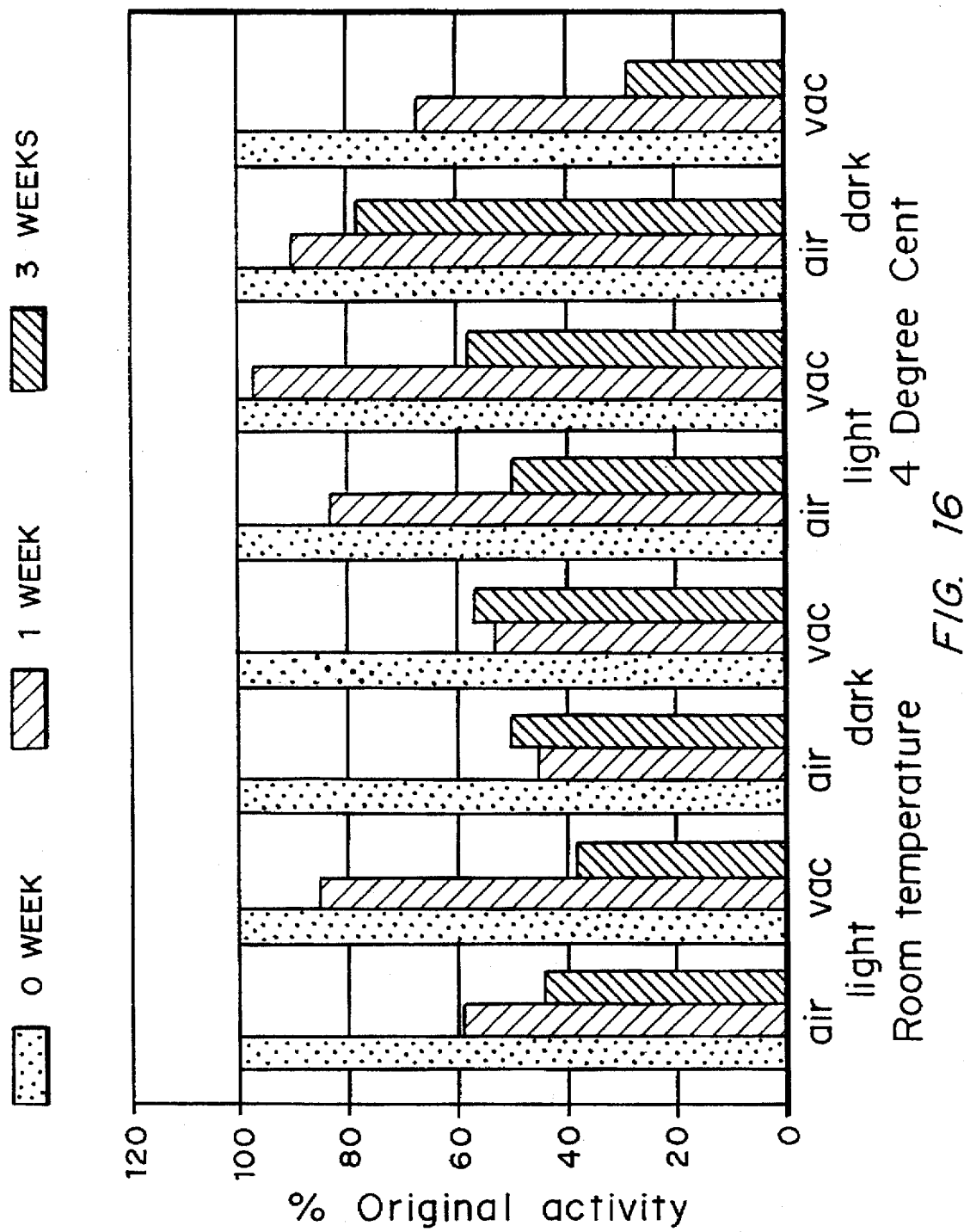
FIG. 16 is a graph illustrating the stability of shanzha in storage (expressed as per cent original activity) for periods of 0, 1, and 3 weeks, with variables including room or 4° C. temperature, light or dark exposure, and air or vacuum conditions.

As shown in FIG. 16, storage at 4° C. was better on average for stability of shanzha. Storage in light or dark or in the presence or absence of air resulted in no significant difference in the stability of the activity.

When shanzha extract was prepared according to the protocol described in FIG. 1, a stable and active preparation was obtained. However, if the water extract of shanzha is not dehydrated properly, an inactive material will result. Specifically, no more than 40 per cent of the liquid should be removed during the rotary evaporation step. If the material is too concentrated, lyophilization will result in a dark brown, flaky compound that is inactive in preventing down regulation of the LDL receptor. An active preparation should be light brown in color and should have a fluffy appearance.

Modifications and variations of the present invention will be obvious to those skilled in the art from the foregoing detailed description.

2. The method of claim 1 wherein an isolated active component of the shanzha is administered to a patient.

3. The method of claim 1, wherein the active component is an extract of the shanzha fruit.

4. The method of claim 3, wherein the active component is extracted from the dried fruit with an alcohol/water mixture, the resulting water extract is extracted with a chloroform/water mixture, the resulting water extract is extracted with an ethylacetate/water mixture, and the resulting water extract contains the active shanzha extract.

5. The method of claim 4, wherein the active component is extracted from the dried fruit with an ethanol/water mixture, the resulting water mixture is extracted with a chloroform/water mixture, the resulting water extract is extracted with an ethylacetate/water mixture, and the resulting ethylacetate extract contains the active shanzha extract.

6. The method of claim 1 wherein the shanzha is whole fruit or fruit juice.

7. The method of claim 1, wherein the shanzha is administered orally.

8. The method of claim 1, wherein the shanzha is administered to a patient with atherosclerosis.

9. The method of claim 1, wherein the shanzha is administered to a patient with hypercholesterolemia.

10. The method of claim 1 comprising administering to the patient a HMG CoA reductase inhibitor.

11. A composition effective when administered to a patient to decrease blood lipids comprising a component present in an organic solvent/water extract of shanzha fruit which is active in hepatocyte cell culture to increase cellular uptake of lipids from the culture media.

12. The composition of claim 11, wherein the active component is extracted from dried shanzha fruit with an alcohol/water mixture, the resulting water extract is extracted with a chloroform/water mixture, the resulting

---

---

We claim:

1. A method of decreasing blood lipid levels comprising administering to a patient in need thereof an effective amount of shanzha to decrease the level of lipid in the blood.

water extract is extracted with an ethylacetate/water mixture, and the resulting water extract contains the active shanzha extract.

13. The composition of claim 11, wherein the active component is extracted from the dried fruit with an ethanol/ water mixture, the resulting water mixture is extracted with a chloroform/water mixture, the resulting water extract is extracted with an ethylacetate/water mixture, and the resulting ethylacetate extract contains the active shanzha extract.

14. The composition of claim 13, wherein the active component is further purified from the other components of the ethyl acetate extract by chromatography.

* * * * *